US006489125B1

(12) United States Patent
Marks et al.

(10) Patent No.: US 6,489,125 B1
(45) Date of Patent: Dec. 3, 2002

(54) METHODS FOR IDENTIFYING CHEMICAL COMPOUNDS THAT INHIBIT DISSOCIATION OF FKBP12.6 BINDING PROTEIN FROM TYPE 2 RYANODINE RECEPTOR

(75) Inventors: Andrew R. Marks, Larchmont; Steven O. Marx, New York, both of NY (US)

(73) Assignee: The Trustees of Columbia University In The City of New York, New York, NY (US)

( * ) Notice: Subject to any disclaimer, the term of this patent is extended or adjusted under 35 U.S.C. 154(b) by 0 days.

(21) Appl. No.: 09/568,474

(22) Filed: May 10, 2000

(51) Int. Cl.[7] .................. G01N 33/53; G01N 33/567; G01N 33/569; C12Q 1/00
(52) U.S. Cl. .................. 435/7.2; 435/4; 435/7.21; 435/7.32; 435/7.31; 435/7.7; 436/501
(58) Field of Search .................. 435/4, 7.2, 7.21, 435/7.31, 7.32, 7.7; 436/501

(56) References Cited

PUBLICATIONS

Brillantes, A.–M. B., Ondriaš, K., Scott, A., Kobrinsky, E., Ondriašová, E., Moschella, M. C., Jayaraman, T., Landers, M., Ehrlich, B. E., and Marks, A. R.(1994). Stabilization of calcium release channel (ryanodine receptor) function by FK506–binding protein. Cell 77, 513–523 (Exhibit 2).
Bristow, M.R., Ginsburg, R., Minobe, W., Cubicciotti, R. S., Sageman, W. S., Lurie, K., Billingham, M.E., Harrison, D.C., and Stinson, E. B. (1982). Decreased catecholamine sensitivity and beta–adrenergic–receptor density in failing human hearts. New Engl. J. Med. 307, 205–211 (Exhibit 3).
Bristow, M.R., Minobe, W., Rasmussen, R., Larrabee, P., Skerl, L., Klein, J. W., Anderson, F. L., Murray, J., Mestroni, L., Karwande, S. V., Fowler, M., and Ginsburg, R. (1992). Beta–adrenergic neuroeffector abnormalities in the failing human heart are produced by local rather than systemic mechanisms. J. Clin. Invest. 89, 803–815 (Exhibit 4).
Cameron, A. M., Nucifora, F. C., Jr., Fung, E. T., Livingston, D. J., Aldape, R. A., Ross, C. A., and Snyder, S. H. (1997). FKBP12 binds the inositol 1,4,5–trisphosphate receptor at leucine–proline (1400–1401) and anchors clacineurin to this FK506–like domain. J. Biol.Chem. 272, 27582–27588 (Exhibit 5).

Chen, Y. G., Liu, F., and Massagué, J. (1997). Mechanism of TGFbeta receptor inhibition by FKBP12. EMBO J. 16, 3866–3876 (Exhibit 6).
Go, L. O., Moschella, M. C., Watras, J., Handa, K.K., Fyfe, B.S., and Marks, A. R. (1995). Differential regulation of two types of intracellular calcium release channels during end–stage heart failure. J. Clin. Invest. 95, 888–894 (Exhibit 7).
Gömez, A. M., Valdivia, H.H., Cheng, H., Lederer, M.R., Santana, L. F., Cannell, M.B., McCune, S. A., Altschuld, R. A., and Lederer, W. J. (1997). Defective excitation–contraction coupling in experimental cardiac hypertrophy and heart failure. Science 276, 800–806 (Exhibit 8).
Hain, J., Onoue, H., Mayrleitner, M., Fleischer, S., and Schindler, H. (1995). Phophorylation modulates the function of the calcium release channel of sarcoplasmic reticulum from cardiac muscle. J. Biol. Chem. 270, 2074–2081 (Exhibit 9).
Jayaraman, T., Brillantes, A.–M. B., Timerman, A. P., Fleischer, S., Erdjument–Bromage, H., Tempst, P., and Marks, A. R. (1992). FK506 binding protein associated with the calcium release channel (ryanodine receptor). J. Biol. Chem. 267, 9474–9477 (Exhibit 10).
Kaftan, E., Marks, A. R., and Ehrlich, B. E. (1996). Effects of rapamycin on ryanodine receptor/$Ca^{2+}$–release channels from cardiac muscle. Circ. Res. 78, 990–997 (Exhibit 11).
Marx, S. O., Ondrias, K., and Marks, A. R. (1998). Coupled gating between individual skeletal muscle $Ca^{2+}$release channels (ryanodine receptors). Science 281, 818–821 (Exhibit 12).
Valdivia, H. H., Kaplan, J. H., Ellis–Davies, G. C. R., and Lederer, W. J. (1995). Rapid adaptation of cardiac ryanodine receptors: modulation by Mg2+ and phophorylation. Science 267, 1997–2000 (Exhibit 13).
Yang, J., Drazba, J. A., Ferguson, D. G., and Bond, M. (1998). A–kinase anchoring protein 100 (AKAP100) is localized in multiple subcellular compartments in the adult rat heart. J Cell. Biol. 142, 511–522 (Exhibit 14).

*Primary Examiner*—Elizabeth Kemmerer
*Assistant Examiner*—Ruixiang Li
(74) *Attorney, Agent, or Firm*—John P. White; Cooper & Dunham LLP

(57) ABSTRACT

This invention provides methods of regulating contraction of a subject's heart and of treating heart failure and cardiac arrhythmia. This invention also provides methods of obtaining compounds that bind to, and activate or inhibit the activation of a type 2 ryanodine (RyR2) receptor, and methods for screening for compounds that alleviate heart disease.

17 Claims, 21 Drawing Sheets

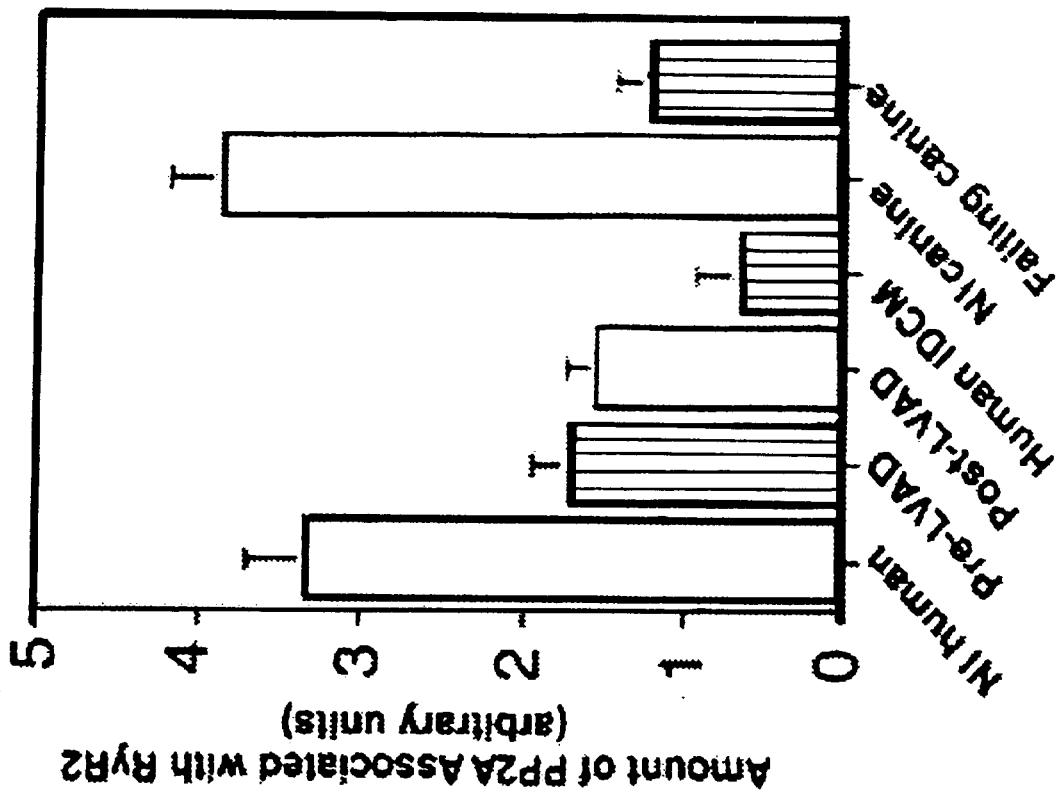
*FIGURE 2D*
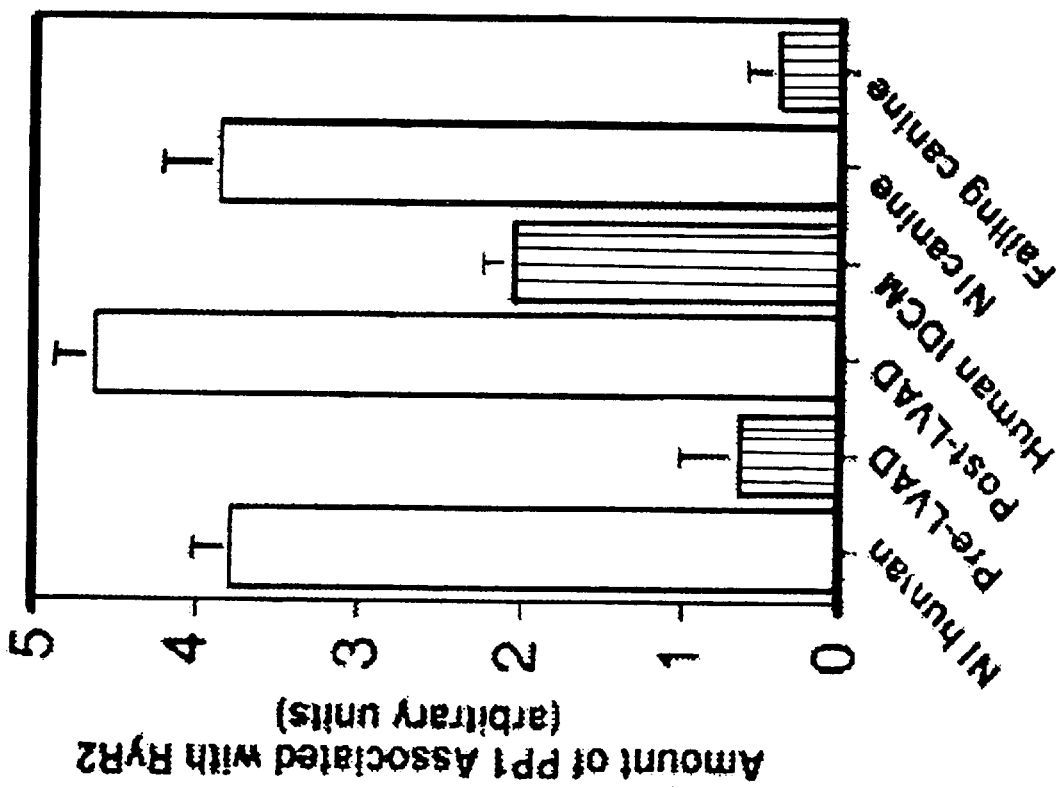

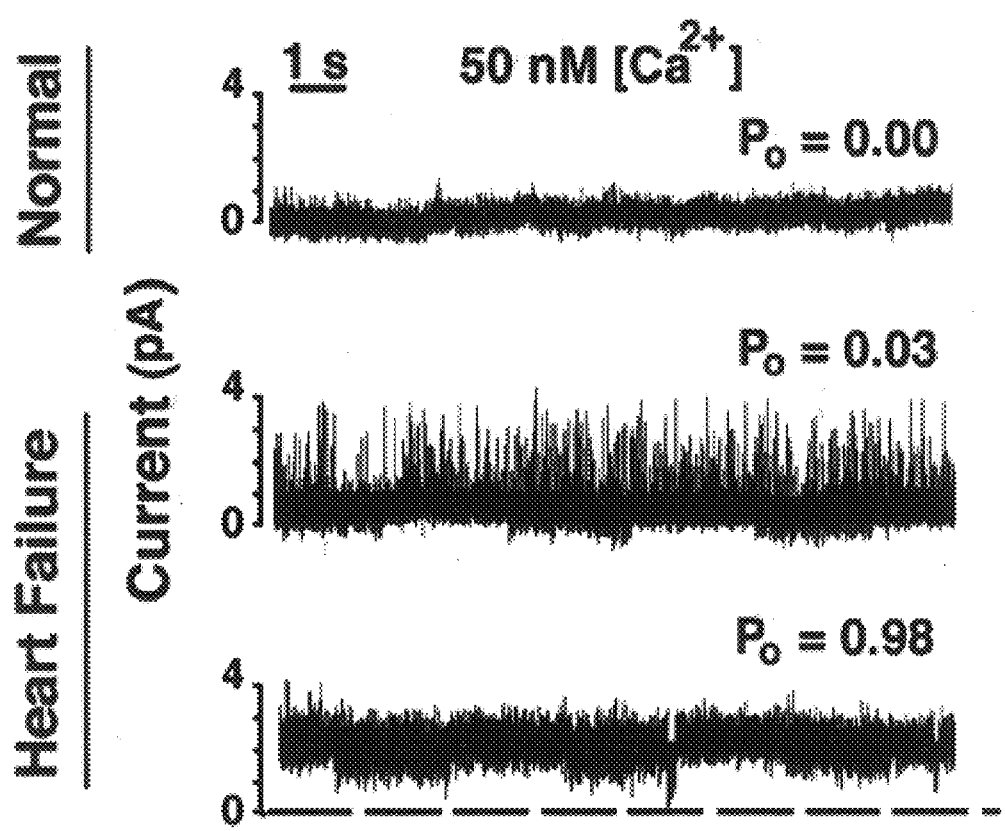

SEQUENCE LISTING

<160> NUMBER OF SEQ ID NOS: 5

<210> SEQ ID NO 1
<211> LENGTH: 15
<212> TYPE: PRT
<213> ORGANISM: Oryctolagus cuniculus
<220> FEATURE:
<221> NAME/KEY: BINDING
<222> LOCATION: (1)..(15)
<223> OTHER INFORMATION: FKBP12 binding site in RyR1, starting at amino acid sequence 2450

<400> SEQUENCE: 1

Ala Leu Arg Ile Arg Ala Ile Leu Arg Ser Leu Val Pro Leu Asp
 1               5                  10                  15

<210> SEQ ID NO 2
<211> LENGTH: 15
<212> TYPE: PRT
<213> ORGANISM: Oryctolagus cuniculus
<220> FEATURE:
<221> NAME/KEY: BINDING
<222> LOCATION: (1)..(15)
<223> OTHER INFORMATION: FKBP12 binding site in RyR2, starting at amino acid sequence 2416

<400> SEQUENCE: 2

Ala Ile Arg Ile Arg Ser Ile Leu Arg Ser Leu Ile Pro Leu Gly
 1               5                  10                  15

<210> SEQ ID NO 3
<211> LENGTH: 15
<212> TYPE: PRT
<213> ORGANISM: Homo sapiens
<220> FEATURE:
<221> NAME/KEY: BINDING

```
<222> LOCATION: (1)..(15)
<223> OTHER INFORMATION: FKBP12 binding site in IP3R1, starting at amino
      acid sequence 1391

<400> SEQUENCE: 3

Asn Val Tyr Thr Glu Ile Lys Cys Asn Ser Leu Leu Pro Leu Asp
 1               5                  10                  15

<210> SEQ ID NO 4
<211> LENGTH: 15
<212> TYPE: PRT
<213> ORGANISM: Homo sapiens
<220> FEATURE:
<221> NAME/KEY: BINDING
<222> LOCATION: (1)..(15)
<223> OTHER INFORMATION: FKBP12 binding site in IP3R2, starting at amino
      acid sequence 1390

<400> SEQUENCE: 4

Asn Val Tyr Thr Glu Ile Lys Cys Asn Ser Leu Leu Pro Leu Asp
 1               5                  10                  15

<210> SEQ ID NO 5
<211> LENGTH: 15
<212> TYPE: PRT
<213> ORGANISM: Homo sapiens
<220> FEATURE:
<221> NAME/KEY: BINDING
<222> LOCATION: (1)..(15)
<223> OTHER INFORMATION: FKBP12 binding site in TbetaRI, starting at
      amino acid sequence 182

<400> SEQUENCE: 5

Tyr Asp Met Thr Thr Ser Gly Ser Gly Ser Gly Leu Pro Leu Leu
 1               5                  10                  15
```

US 6,489,125 B1

METHODS FOR IDENTIFYING CHEMICAL COMPOUNDS THAT INHIBIT DISSOCIATION OF FKBP12.6 BINDING PROTEIN FROM TYPE 2 RYANODINE RECEPTOR

The invention disclosed herein was made with Government support under grant numbers RO1 HL61503, RO1 HL56180, RO1 AI39794, and RO3 TW00949 from the National Institutes of Health, U.S. Department of Health and Human Services. Accordingly, the U.S. Government has certain rights in this invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The contraction of striated muscle is initiated when calcium ($Ca^{2+}$) is released from tubules within the muscle cell known as the sarcoplasmic reticulum (SR). Calcium release channels (ryanodine receptors) on the sarcoplasmic reticulum are required for excitation-contraction (EC) coupling. The type 2 ryanodine receptor (RyR2) is found in the heart, while the type 1 ryanodine receptor (RyR1) is found in skeletal muscle. The RyR2 receptor is a tetramer comprised of four 565,000 dalton RyR2 polypeptides and four 12,000 dalton FK-506 binding proteins (FKBP12.6). FKBP12s are regulatory subunits that stabilize RyR channel function (Brillantes et al., 1994) and facilitate coupled gating between neighboring RyR channels (Marx et al., 1998) which are packed into dense arrays. in specialized regions of the sarcoplasmic reticulum that release intracellular stores of $Ca^{2+}$ triggering muscle contraction.

RyRs are ligand activated channels, and $Ca^{2+}$ is the important physiological ligand that activates the channels in cardiac muscle during excitation-contraction coupling. The $Ca^{2+}$-dependence of RyR channel activity is biphasic such that low cytosolic $Ca^{2+}$ concentration ($\mu$M) activates the channels and high $Ca^{2+}$ concentration (mM) inactivates the channels (Bezprozvanny et al., 1991). One FKBP12 molecule is bound to each RyR subunit. Dissociation of FKBP12 significantly alters the biophysical properties of the channels resulting in the appearance of subconductance states, and increased open probability (Po) due to an increased sensitivity to $Ca^{2+}$-dependent activation (Brillantes et al., 1994; Kaftan et al., 1996). In addition, dissociation of FKBP12 from RyR channels inhibits coupled gating of RyR channels resulting in channels that gate stochastically rather than as an ensemble (Marx et al., 1998). Coupled gating of arrays of RyR channels is thought to be important for efficient excitation-contraction coupling that regulates muscle contraction (Marx et al., 1998).

FKBPs are cis-trans peptidyl-prolyl isomerases that are widely expressed and subserve a variety of cellular functions (Marks, 1996). FKBP12s are tightly bound to and regulate the function of the skeletal (RyR1) (Brillantes et al., 1994; Jayaraman et al., 1992) and cardiac (RyR2) (Kaftan et al., 1996) muscle $Ca^{2+}$ release channels, as well as a related intracellular $Ca^{2+}$ release channel known as the type 1 inositol 1,4,5-trisphosphate receptor (IP3R1) (Cameron et al., 1997), and the type I transforming growth factor $\beta$ (TGF$\beta$) receptor (T$\beta$RI) (Chen et al., 1997).

The present application discloses the following. Protein kinase A (PKA) phosphorylation regulates the binding of FKBP12.6 to the RyR channel both in vitro and in vivo. PKA phosphorylation of the cardiac $Ca^{2+}$ release channel (RyR2) on the sarcoplasmic reticulum dissociates the regulatory subunit FKBP12.6 from the RyR2 channel resulting in altered channel function manifested as an increased open probability, increased sensitivity to $Ca^{2+}$-induced activation, and destabilization of the RyR2 channel resulting in subconductance states. RyR2 PKA phosphorylation is physiologically regulated in vivo. RyR2 channels from failing hearts were PKA hyperphosphorylated and exhibited decreased binding of the FKBP12.6 regulatory subunit resulting in the same severe defects in single channel properties observed in in vitro PKA hyperphosphorylated RyR2 channels. The RyR2 channel comprises a macromolecular complex that includes the regulatory subunit FKBP12.6, protein kinase A (PKA), the PKA regulatory subunit RII, protein phosphatase 2A (PP2A), protein phosphatase 1 (PP1), and muscle A kinase anchoring protein (mAKAP). Taken together these data demonstrate that local regulation of the RyR2 channel via PKA phosphorylation is a potent mechanism for modulating $Ca^{2+}$ release from the cardiac sarcoplasmic reticulum. Dysregulation of this control mechanism occurs in failing hearts and can explain the observed defects in excitation-contraction coupling that contribute to cardiac dysfunction. Methods for treating heart disease are disclosed, as are methods for screening for compounds that alleviate heart disease.

SUMMARY OF THE INVENTION

This invention is directed to a method of regulating contraction of a subject's heart by administering to the subject a compound which regulates protein kinase A (PKA) phosphorylation of a type 2 ryanodine (RyR2) receptor of the subject's heart.

This invention provides a method of treating a subject's heart failure by administering to the subject a compound which decreases protein kinase A (PKA) phosphorylation of a type 2 ryanodine (RyR2) receptor of the subject's heart, thereby alleviating the subject's heart failure. This invention also provides a method of treating a subject's heart failure by administering to the subject a compound which decreases dissociation of a FKBP12.6 binding protein from a type 2 ryanodine (RyR2) receptor of the subject's heart, thereby alleviating the subject's heart failure. This invention in addition provides a method of treating a subject's heart failure by administering to the subject a compound which mimics binding of a FKBP12.6 binding protein to a type 2 ryanodine (RyR2) receptor of the subject's heart, thereby alleviating the subject's heart failure.

This invention provides a method of treating a subject's cardiac arrhythmia by administering to the subject a compound which decreases protein kinase A (PKA) phosphorylation of a type 2 ryanodine (RyR2) receptor of the subject's heart, thereby alleviating the subject's cardiac arrhythmia. This invention also provides a method of treating a subject's cardiac arrhythmia by administering to the subject a compound which decreases dissociation of a FKBP12.6 binding protein from a type 2 ryanodine (RyR2) receptor of the subject's heart, thereby alleviating the subject's cardiac arrhythmia. This invention in addition provides a method of treating a subject's cardiac arrhythmia by administering to the subject a compound which mimics binding of a FKBP12.6 binding protein to a type 2 ryanodine (RyR2) receptor of the subject's heart, thereby alleviating the subject's cardiac arrhythmia.

This invention provides a method for identifying a chemical compound which specifically binds to a type 2 ryanodine (RyR2) receptor, which comprises contacting cells expressing the RyR2 receptor with the chemical compound under conditions suitable for binding and detecting specific binding of the chemical compound to the RyR2 receptor. This invention also provides a method for identifying a chemical compound which specifically binds to a type 2 ryanodine (RyR2) receptor, which comprises contacting a fraction containing sacroplasmic reticulum or endoplasmic reticulum from a cell extract of cells expressing the RyR2 receptor, with the chemical compound under conditions suitable for binding and detecting specific binding of the chemical compound to the RyR2 receptor.

This invention provides a method involving competitive binding for identifying a chemical compound which specifically binds to a type 2 ryanodine (RyR2) receptor, which comprises separately contacting cells expressing the RyR2 receptor, with both the chemical compound and a second chemical compound known to bind to the RyR2 receptor, and with only the second chemical compound, under conditions suitable for binding of both compounds, and detecting specific binding of the chemical compound to the RyR2 receptor, a decrease in binding of the second chemical compound to the RyR2 receptor in the presence of the chemical compound indicating that the chemical compound binds to the RyR2 receptor. This invention also provides a method involving competitive binding for identifying a chemical compound which specifically binds to a type 2 ryanodine (RyR2) receptor, which comprises separately contacting a fraction containing sacroplasmic reticulum or endoplasmic reticulum from a cell extract of cells expressing the RyR2 receptor, with both the chemical compound and a second chemical compound known to bind to the RyR2 receptor, and with only the second chemical compound, under conditions suitable for binding of both compounds, and detecting specific binding of the chemical compound to the RyR2 receptor, a decrease in binding of the second chemical compound to the RyR2 receptor in the presence of the chemical compound indicating that the chemical compound binds to the RyR2 receptor.

This invention provides a method of screening a plurality of chemical compounds not known to bind to a type 2 ryanodine (RyR2) receptor to identify a compound which specifically binds to the RyR2 receptor, which comprises:

(a) contacting cells expressing the RyR2 receptor with a compound known to bind specifically to the RyR2 receptor;

(b) contacting the cells of step (a) with the plurality of compounds not known to bind specifically to the RyR2 receptor, under conditions permitting binding of compounds known to bind to the RyR2 receptor;

(c) determining whether the binding of the compound known to bind to the RyR2 receptor is reduced in the presence of the plurality of compounds, relative to the binding of the compound in the absence of the plurality of compounds; and if so (d) separately determining the binding to the RyR2 receptor of each compound included in the plurality of compounds, so as to thereby identify any compound included therein which specifically binds to the RyR2 receptor.

This invention also provides a method of screening a plurality of chemical compounds not known to bind to a type 2 ryanodine (RyR2) receptor to identify a compound which specifically binds to the RyR2 receptor, which comprises:

(a) contacting a fraction containing sacroplasmic reticulum or endoplasmic reticulum from a cell extract of cells expressing the RyR2 receptor with a compound known to bind specifically to the RyR2 receptor;

(b) contacting the fraction of step (a) with the plurality of compounds not known to bind specifically to the RyR2 receptor, under conditions permitting binding of compounds known to bind to the RyR2 receptor;

(c) determining whether the binding of the compound known to bind to the RyR2 receptor is reduced in the presence of the plurality of compounds, relative to the binding of the compound in the absence of the plurality of compounds; and if so (d) separately determining the binding to the RyR2 receptor of each compound included in the plurality of compounds, so as to thereby identify any compound included therein which specifically binds to the RyR2 receptor.

This invention provides a method for determining whether a chemical compound activates a type 2 ryanodine (RyR2) receptor, which comprises contacting cells expressing the RyR2 receptor with the chemical compound under conditions suitable for activation of the RyR2 receptor and measuring RyR2 receptor activation in the presence and in the absence of the chemical compound, an increase in RyR2 receptor activation in the presence of the chemical compound indicating that the chemical compound activates the RyR2 receptor. This invention also provides a method for determining whether a chemical compound activates a type 2 ryanodine (RyR2) receptor, which comprises contacting a fraction containing sacroplasmic reticulum or endoplasmic reticulum from a cell extract of cells expressing the RyR2 receptor with the chemical compound under conditions suitable for activation of the RyR2 receptor and measuring RyR2 receptor activation in the presence and in the absence of the chemical compound, an increase in RyR2 receptor activation in the presence of the chemical compound indicating that the chemical compound activates the RyR2 receptor.

This invention provides a method of screening a plurality of chemical compounds not known to activate a type 2 ryanodine (RyR2) receptor to identify a compound which activates the RyR2 receptor which comprises:

(a) contacting cells expressing the RyR2 receptor with the plurality of compounds not known to activate the RyR2 receptor, under conditions permitting activation of the RyR2 receptor;

(b) determining whether the activity of the RyR2 receptor is increased in the presence of one or more of the compounds; and if so (c) separately determining whether the activation of the RyR2 receptor is increased by any compound included in the plurality of compounds, so as to thereby identify each compound which activates the RyR2 receptor.

This invention also provides a method of screening a plurality of chemical compounds not known to activate a type 2 ryanodine (RyR2) receptor to identify a compound which activates the RyR2 receptor which comprises:

(a) contacting a fraction containing sacroplasmic reticulum or endoplasmic reticulum from a cell extract of cells expressing the RyR2 receptor with the plurality of compounds not known to activate the RyR2 receptor, under conditions permitting activation of the RyR2 receptor;

(b) determining whether the activity of the RyR2 receptor is increased in the presence of one or more of the compounds; and if so (c) separately determining whether the activation of the RyR2 receptor is increased by any compound included in the plurality of compounds, so as to thereby identify each compound which activates the RyR2 receptor.

This invention provides a method for determining whether a chemical compound inhibits activation of a type 2 ryanodine (RyR2) receptor, which comprises separately contacting cells expressing the RyR2 receptor with both the chemical compound and a second chemical compound known to activate the RyR2 receptor, and with only the second chemical compound, under conditions suitable for activation of the RyR2 receptor, and measuring RyR2 receptor activation in the presence of only the second chemical compound and in the presence of both the second chemical compound and the chemical compound, a smaller RyR2 receptor activation in the presence of both the chemical compound and the second chemical compound than in the presence of only the second chemical compound indicating that the chemical compound inhibits activation of the RyR2 receptor. This invention also provides a method for determining whether a chemical compound inhibits activation of a type 2 ryanodine (RyR2) receptor, which comprises separately contacting a fraction containing sacroplasmic reticulum or endoplasmic reticulum from a cell extract of cells expressing the RyR2 receptor with both the chemical compound and a second chemical compound known to activate the RyR2 receptor, and with only the second chemical compound, under conditions suitable for activation of the RyR2 receptor, and measuring RyR2 receptor activation in the presence of only the second chemical compound and in the presence of both the second chemical compound and the chemical compound, a smaller RyR2 receptor activation in the presence of both the chemical compound and the second chemical compound than in the presence of only the second chemical compound indicating that the chemical compound inhibits activation of the RyR2 receptor.

This invention provides a method of screening a plurality of chemical compounds not known to inhibit the activation of a type 2 ryanodine (RyR2) receptor to identify a compound which inhibits the activation of the RyR2 receptor, which comprises:

(a) contacting cells expressing the RyR2 receptor with the plurality of compounds in the presence of a known RyR2 receptor activator, under conditions permitting activation of the RyR2 receptor;

(b) determining whether the amount of activation of the RyR2 receptor is reduced in the presence of one or more of the compounds, relative to the amount of activation of the RyR2 receptor in the absence of such one or more compounds; and if so (c) separately determining whether each such compound inhibits activation of the RyR2 receptor for each compound included in the plurality of compounds, so as to thereby identify any compound included in such plurality of compounds which inhibits the activation of the RyR2 receptor.

This invention also provides a method of screening a plurality of chemical compounds not known to inhibit the activation of a type 2 ryanodine (RyR2) receptor to identify a compound which inhibits the activation of the RyR2 receptor, which comprises:

(a) contacting a fraction containing sacroplasmic reticulum or endoplasmic reticulum from a cell extract of cells expressing the RyR2 receptor with the plurality of compounds in the presence of a known RyR2 receptor activator, under conditions permitting activation of the RyR2 receptor;

(b) determining whether the amount of activation of the RyR2 receptor is reduced in the presence of one or more of the compounds, relative to the amount of activation of the RyR2 receptor in the absence of such one or more compounds; and if so (c) separately determining whether each such compound inhibits activation of the RyR2 receptor for each compound included in the plurality of compounds, so as to thereby identify any compound included in such plurality of compounds which inhibits the activation of the RyR2 receptor.

This invention provides a chemical compound identified by any of the methods described herein.

This invention provides a method for making a composition of matter which comprises identifying a chemical compound using any of the methods described herein, and then synthesizing the chemical compound or a novel structural and functional analog or homolog thereof.

This invention provides a pharmaceutical composition comprising (a) an amount of a chemical compound identified using any of the methods described herein, or a novel structural and functional homolog or analog thereof, capable of passing through a cell membrane and effective to activate, or inhibit the activation of, a RyR2 receptor and (b) a pharmaceutically acceptable carrier capable of passing through the cell membrane.

This invention provides a method for preparing a composition which comprises admixing a carrier and a pharmaceutically effective amount of a chemical compound identified by any of the methods described herein or a novel structural and functional anaolog or homolog thereof.

This invention provides a method of treating a subject with a heart disease which comprises administering to the subject a therapeutically effective amount of a chemical compound identified by any of the methods described herein.

This invention provides the use of a chemical compound identified by any of the methods described herein for the preparation of a pharmaceutical composition for treating an abnormality, wherein the abnormality is alleviated by activating, or by inhibiting the activation of, a RyR2 receptor.

Figure 1A:
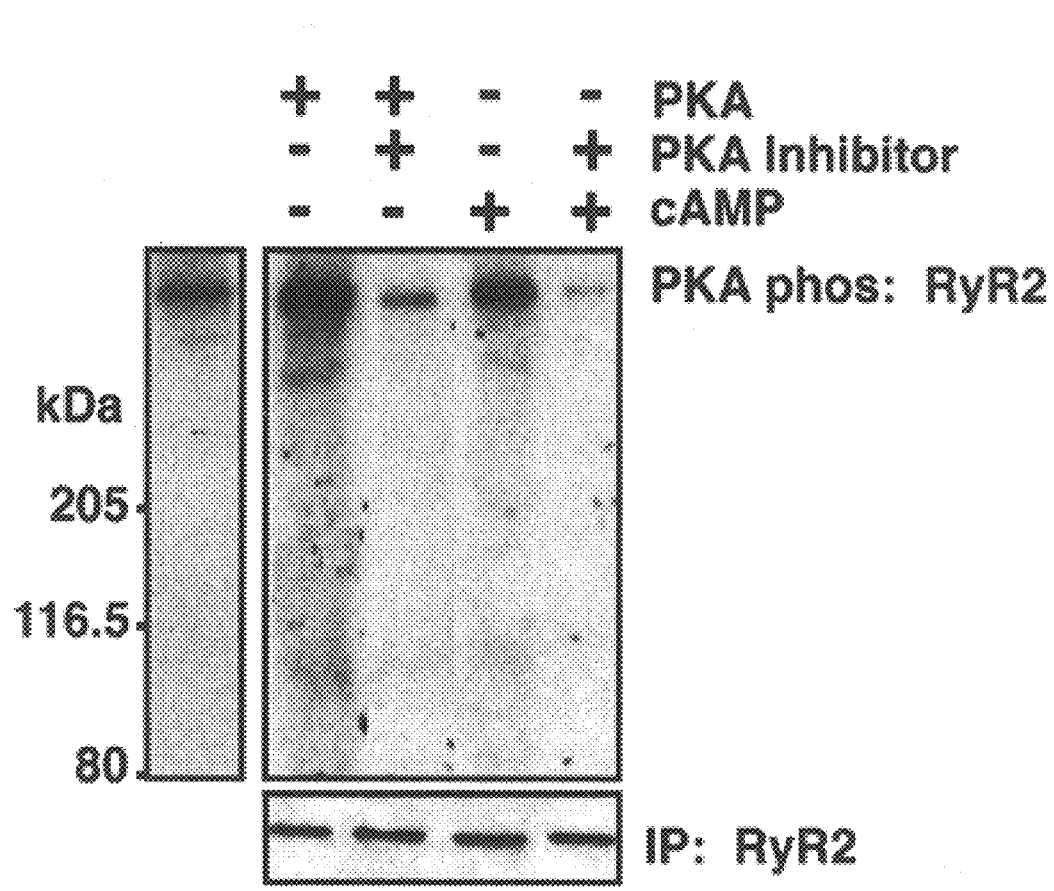
FIG. 1. PKA phosphorylation of RyR2, a macromolecular signaling complex.

A) RyR2 was phosphorylated by addition of PKA (5 units) or 3,5'-cyclic adenosine 5'-monophosphate (cAMP) (10 $\mu$M); the PKA inhibitor $PKI_{5-24}$ (500 nM) inhibited the phosphorylation. RyR2 was immunoprecipitated and subjected to in vitro kinasing reactions; equivalent amounts of RyR2 protein were used in each reaction as shown by immunoblotting.

B) RyR2 channels were isolated using [$^3$H] ryanodine by centrifugation on a sucrose density gradient as described by Brillantes et al. (1994). Both [$^3$H] ryanodine binding (open squares) and total protein (filled circles) were plotted. Individual RyR2 channels sediment at 30S (arrow), and two or more physically attached RyR2 channels sediment in higher sucrose fractions as previously reported for RyR1 channels (Marx et al., 1998).

C) Immunoblotting gradient fractions with specific antibodies showed that FKBP12.6, PKA catalytic subunit (PKA cat), PKA regulatory subunit (RII), protein phosphatase 2A (PP2A), protein phosphatase 1 (PP1), muscle A-kinase anchoring protein (mAKAP), but not calcineurin (CnA), were detected in all fractions containing RyR2.

D) RyR2 binding to microcystin-sepharose beads was competed using free microcystin-LR. Samples were pelleted and analyzed by SDS-PAGE and immunoblotting with anti-RyR antibody.

E) Components of the RyR2 complex (FKBP12.6, PKA, RII, PP2A, PP1, and mAKAP) were co-immunoprecipitated from cardiac SR (200 μg). The RyR2 complex was sedimented using microcystin-sepharose, the complex was competed off with free microcystin-LR followed by immunoprecipitation with anti-RyR antibody (αRyR) and immunoblotting. Positive controls (+Cont.) were recombinant or purified proteins as indicated; negative controls (−Cont.) were blocking peptides for each antibody or pre-absorbing the antibodies with purified or recombinant proteins. In all cases data shown are representative of more than three similar experiments.

FIG. 2. RyR2 PKA phosphorylation during heart failure.

A) PKA back-phosphorylation of RyR2 protein immunoprecipitated from the indicated tissues are shown in the top row; the middle row shows the amount of RyR2 immunoprecipitated in each reaction; and the bottom row shows the amount of PKA co-immunoprecipitated with RyR2 from each sample. Normal, non-failing human heart; ICM, end-stage failing human heart with ischemic cardiomyopathy; IDCM, end-stage failing human heart with idiopathic dilated cardiomyopathy; IDCM(−Dba) samples from patients not treated with a β-adrenergic agonist Dba (dobutamine); Pre-LVAD, left ventricular sample taken from a human heart with end-stage failure during insertion of a left ventricular assist device (LVAD); Post-LVAD, sample from the same human heart after LVAD treatment; PKI, representative negative control showing that PKA phosphorylation was inhibited by PKI.

B) Quantitation of RyR2 back-phosphorylation studies shown in (A). The inset shows PKA hyperphosphorylation of RyR2 confirmed by anti-phosphoserine immunoblotting: 1) top row, RyR2 immunoblot (top lanes); 2) bottom row, anti-phosphoserine immunoblotting of the same samples. Lane 1, normal non-failing human heart; lane 2, failing human (ICM) heart. For each condition a minimum of three experiments using tissue from three different hearts were performed, error bars represent standard deviation of the mean.

C) PP1 and PP2A co-immunoprecipitated with RyR2 from normal and failing hearts. Following immunoprecipitation with anti-RyR antibody, immunoprecipitates were size fractionated and immunoblotted with: anti-RyR2 (top panel), anti-PP1 (middle panel), or anti-PP2A antibodies. Data shown are representative of three similar experiments.

D) The amount of PP1 and PP2A co-immunoprecipitating with RyR2 was determined by densitometric quantitation of the immunoblots and normalized for the amount of RyR2 co-immunoprecipitated. Less PP1 and PP2A were associated with RyR2 in all of the heart failure samples. Data shown are representative of three similar experiments.

FIG. 3. Mapping signaling complex binding sites on RyR2.

A) The FKBP12.6 binding site in RyR2 was identified using a yeast two-hybrid interaction screen. The left bar-graph shows β-galactosidase activity for yeast transformed with: 1) FKBP12.6/activation domain fusion protein alone; 2) RyR2 (residues 2361–2496)/DNA binding domain alone; 3) both together. Interaction between FKBP12.6 and an RyR2 fragment (residues 2361–2496, Otsu et al., 1990) activates Gal-4 transcription resulting in increased β-galactosidase activity. The bar-graph shows normalized β-galactosidase activity for rapamycin-resistant yeast transformed with FKBP12.6 and the RyR2 fragment treated with the indicated concentrations of rapamcyin which competes FKBP12.6 off from RyR2. The FKBP12/12.6 binding site in RyR2 is defined by isoleucine 2427 and proline 2428 (arrow). Shown in the box are sequences of FKBP12 binding sites in RyR1 (SEQ ID NO: 1) (Takeshima, et al., 1989), RyR2 (SEQ ID NO: 2) (Otsu et al., 1990), IP3R1 (SEQ ID NO: 3) (Harnick et al., 1995), IP3R2 (SEQ ID NO: 4) (Yamamoto-Hino et al., 1994), and TβRI (SEQ ID NO: 5) (Franzen et al., 1993).

B) Glutathione S Transferase (GST)-RyR2 fusion proteins bound to sepharose beads were incubated with cardiac SR (200 μg), pelleted, size fractionated by SDS-PAGE and immunoblotted with the indicated antibodies. Lane 1, positive control (recombinant proteins); lane 2, sepharose beads (negative control); lane 3, GST (negative control); lane 4, GST-RyR2-1-334 (amino acid residues 1-334); lane 5, GST-RyR2-513-808; lane 6, GST-RyR2-1027-1304; lane 7, GST-RyR2-1251-1500; lane 8, GST-RyR2-1451-1768.

C) Immunohistochemistry showing co-localization of mAKAP and RyR2 to cardiac SR in normal and failing human hearts. Bars: long, 1.5 μm; short 5 μm.

D) In vitro kinasing reactions using GST-RyR2 fusion proteins containing the wild type (WT) and mutant (S2809A) PKA site. PKA phosphorylation was performed with [$\gamma^{32}$P]-ATP followed by size fractionation on SDS-PAGE and autoradiography.

FIG. 4. PKA phosphorylation of RyR2 inhibits FKBP12.6 binding.

A) FKBP12.6 was co-immunoprecipitated from cardiac SR using an anti-RyR antibody followed by immunoblotting with either anti-RyR (top panel) or anti-FKBP (bottom panel) antibodies. The indicated immunoprecipitates were phosphorylated with PKA prior to size fractionation by SDS-PAGE. Co-immunoprecipitation of FKBP12.6 with RyR2 was significantly reduced in the PKA phosphorylated samples but not in $Ca^{2+}$-calmodulin kinase (CaMKII) or protein kinase C (PKC) phosphorylated RyR2 samples. RyR2 phosphorylation, as assessed using [$\gamma^{32}$P]-ATP, was equivalent for PKA, CamKII and PKC (not shown).

B) Quantitation of the amount of FKBP12.6 co-immunoprecipitating with RyR2 from the indicated samples. Normal human heart; pre-LVAD, left ventricular sample taken from a human heart with end-stage failure during insertion of a left ventricular assist device; Post-LVAD, sample from the same human heart after LVAD treatment; IDCM, end-stage failing human heart with idiopathic dilated cardiomyopathy; normal non-failing canine heart; canine rapid pacing-induced heart failure model. Inset shows representative co-immunoprecipitations of RyR2 and FKBP12.6 using an anti-RyR antibody: lane 1, normal human heart; lane 2, pre-LVAD; lane 3, post-LVAD; lane 4, human IDCM; lane 5, normal canine heart; lane 6, failing canine heart. There was significantly less FKBP12.6 co-immunoprecipitated with RyR2 in each of the failing hearts compared to normals. Data shown are representative of three or more similar experiments. FKBP12.6 amounts were quantified using densitometry of the specific FKBP12.6 band on a single immunoblot for each experiment.

FIG. 5. PKA phosphorylation activates RyR2 and induces subconductance states.

A) Open probability ($P_o$) of a single RyR2 channel plotted as a function of time showing the effect of MgATP (2 mM) followed by addition of PKA (2 units).

B) Single channel tracings corresponding to the experiment shown in A. Channel openings are in the upward direction, the current amplitude for a fully open channel under these conditions ($Ba^{2+}$ as current carrier) was ~4 pA. Increased $P_o$ and multiple subconductance states are seen after PKA addition. Corresponding amplitude histograms are shown at the right of the tracings for channels before and after PKA treatment. The subconductance states have current amplitudes of 1, 2, or 3 pA, corresponding to ¼, ½ and ¾ of the full conductance of the channel as previously described for channels in the absence of FKBP12 (Brillantes et al., 1994; Marx et al., 1998). The bottom tracing shows the characteristic modification of the RyR2 channels by ryanodine (1 $\mu$M) which locks the PKA phosphorylated RyR2 channel in a one-half conductance state. Recordings were at 0 mV potential across the lipid bilayer membrane; the dashed lines indicate the closed state of the channels. Data shown are representative of 4 experiments using SR microsomes containing RyR2 isolated from 2 different dogs (2 separate isolations for each animal). Similar results were obtained using RyR2 channels isolated from normal human heart.

FIG. 6. Defective RyR2 channels and contractility in failing heart muscle.

A) Single channel tracings of RyR2 from: normal canine heart (top three tracings); failing canine heart (bottom three tracings). Corresponding amplitude histograms are at right. The bottom tracing in each set of three shows the characteristic modification of the RyR2 channels by ryanodine (1 $\mu$M) which locks the channel in a ½ conductance state. Recordings were at 0 mV; the dashed lines indicate the closed state of the channels. Similar results were obtained using RyR2 channels isolated from failing human hearts (see text for details).

B) RyR2 channels from failing canine hearts exhibited increased sensitivity to $Ca^{2+}$-dependent activation compared to channels from normal hearts which were generally inactive at $\leq$50 nM free $Ca^{2+}$ in the cis (cytoplasmic) chamber (top tracing). RyR2 channels from failing hearts exhibited two types of $Ca^{2+}$-dependent activation at $\leq$50 nM free $Ca^{2+}$. Some channels from failing hearts (n=15) were active with a low $P_o$ (second tracing) at $\leq$50 nM free $Ca^{2+}$; others (n=4) were extremely active at $\leq$50 nM free $Ca^{2+}$ remaining stably open in a subconductance state (bottom tracing). Similar results were obtained using RyR2 channels isolated from failing human hearts.

C) Continuous force tracings from human left ventricular trabeculae during exposure to isoproterenol (4 $\mu$M). Normal heart sample showed >3-fold increase in force following isoproterenol. Muscles from patients with congestive heart failure (CHF) showed either no response in patients receiving $\beta$-agonists prior to transplant, or a blunted response (~2-fold increase) in patients not receiving $\beta$-agonists prior to transplant. Muscle obtained from the apical core tissue of an LVAD recipient receiving $\beta$-agonist prior to surgery showed almost no response to isoproterenol. However, muscle obtained from the same patient after 64 days of LVAD support shows a >5-fold increase in response to isoproterenol (n=3, p<0.01).

Figure 7:
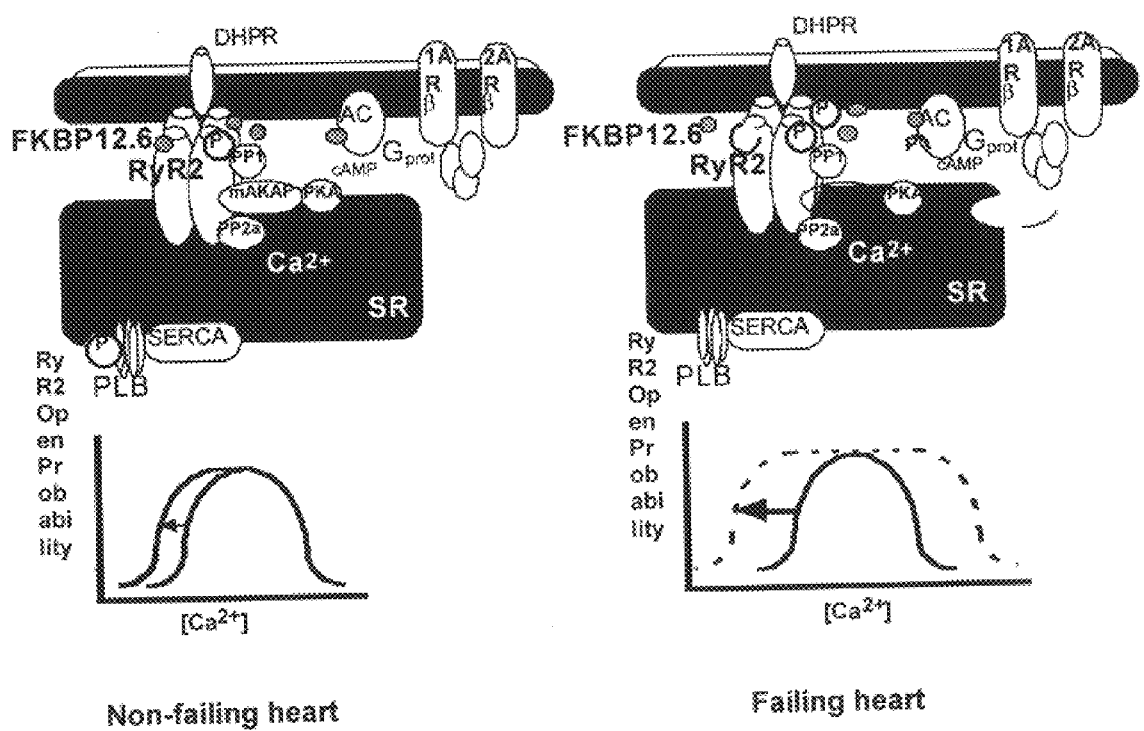

FIG. 7. Model of the affects of PKA phosphorylation of RyR2 in the heart. In the non-failing heart (left panel) $\beta$-agonists bind to receptors ($\beta$1 and $\beta$2 adrenergic receptors, AR) coupled to heterotrimeric G-proteins (Gprot) which in turn activate adenylyl cyclase (AC) raising cyclic AMP (cAMP) levels and activating PKA. In this model PKA phosphorylation of RyR2 induces dissociation of one FKBP12.6 from the channel shifting the $Ca^{2+}$-dependence for activation to the left, increasing the sensitivity of the RyR2 to activation by $Ca^{2+}$ influx via the voltage-gated calcium channel in the T-tubule (dihydropyridine receptor, DHPR) and increasing RyR2 channel open probability. The result is increased SR $Ca^{2+}$ release and cardiac contractility. The tetrameric RyR2 channel is part of a macromolecular signaling complex that includes four molecules each of RyR2, FKBP12.6, PKA, protein phosphatases PP1 and PP2A, and the anchoring protein mAKAP (the PKA, PP1, PP2A, mAKAP components of the macromolecular complex are shown for only one of the four RyR2 subunits). $Ca^{2+}$ reuptake into the SR occurs via the SR $Ca^{2+}$-ATPase (SERCA) and its associated regulatory protein phospholamban (PLB).

In failing hearts (right panel) PKA hyperphosphorylation of RyR2 may contribute to the blunted response to $\beta$-agonists observed in failing heart muscle because the channels cannot be further PKA phosphorylated. RyR2 channels in failing hearts exhibit a shift in the $Ca^{2+}$-dependence for activation such that they are activated at resting levels of cytosolic $Ca^{2+}$.

DETAILED DESCRIPTION OF THE INVENTION

The following definitions are presented as an aid in understanding this invention.

As used herein a RyR2 receptor means a type 2 ryanodine receptor, which is a calcium ($Ca^{2+}$) release channel on the sarcoplasmic reticulum (SR) of the heart.

FKBP12.6 means a 12,000 dalton FK-506 binding protein. FKBP12.6 is bound to and regulates the function of the RyR2 receptor channel.

PKA phosphorylation means a reaction in which a phosphate group is substituted for a hydroxyl group by the enzyme protein kinase A (PKA).

Back-phosphorylation of the RyR2 receptor means the in vitro phosphorylation of RyR2 by protein kinase A.

Having due regard to the preceding definitions, the present invention is directed to a method of regulating contraction of a subject's heart by administering to the subject a compound which regulates protein kinase A (PKA) phosphorylation of a type 2 ryanodine (RyR2) receptor of the subject's heart. In one embodiment, PKA phosphorylation of the RyR2 receptor causes dissociation of a FKBP12.6 binding protein from the RyR2 receptor.

This invention provides a method of treating a subject's heart failure by administering to the subject a compound which decreases protein kinase A (PKA) phosphorylation of a type 2 ryanodine (RyR2) receptor of the subject's heart, thereby alleviating the subject's heart failure. In one embodiment, PKA phosphorylation of the RyR2 receptor causes dissociation of a FKBP12.6 binding protein from the RyR2 receptor.

This invention also provides a method of treating a subject's heart failure by administering to the subject a compound which decreases dissociation of a FKBP12.6 binding protein from a type 2 ryanodine (RyR2) receptor of the subject's heart, thereby alleviating the subject's heart failure. This invention in addition provides a method of treating a subject's heart failure by administering to the subject a compound which mimics binding of a FKBP12.6 binding protein to a type 2 ryanodine (RyR2) receptor of the subject's heart, thereby alleviating the subject's heart failure.

This invention provides a method of treating a subject's cardiac arrhythmia by administering to the subject a compound which decreases protein kinase A (pKA) phosphorylation of a type 2 ryanodine (RyR2) receptor of the subject's heart, thereby alleviating the subject's cardiac arrhythmia. In one embodiment, PKA phosphorylation of the RyR2 receptor causes dissociation of a FKBP12.6 binding protein from the RyR2 receptor. In one embodiment, the cardiac arrhythmia is a ventricular fibrillation. In another embodiment, the cardiac arrhythmia is a ventricular tachycardia.

This invention also provides a method of treating a subject's cardiac arrhythmia by administering to the subject a compound which decreases dissociation of a FKBP12.6 binding protein from a type 2 ryanodine (RyR2) receptor of the subject's heart, thereby alleviating the subject's cardiac arrhythmia. In one embodiment, the cardiac arrhythmia is a ventricular fibrillation. In another embodiment, the cardiac arrhythmia is a ventricular tachycardia. This invention in addition provides a method of treating a subject's cardiac arrhythmia by administering to the subject a compound which mimics binding of a FKBP12.6 binding protein to a type 2 ryanodine (RyR2) receptor of the subject's heart, thereby alleviating the subject's cardiac arrhythmia. In one embodiment, the cardiac arrhythmia is a ventricular fibrillation. In another embodiment, the cardiac arrhythmia is a ventricular tachycardia.

This invention provides a method for identifying a chemical compound which specifically binds to a type 2 ryanodine (RyR2) receptor, which comprises contacting cells expressing the RyR2 receptor, or contacting a fraction containing sacroplasmic reticulum or endoplasmic reticulum from a cell extract of said cells, with the chemical compound under conditions suitable for binding and detecting specific binding of the chemical compound to the RyR2 receptor.

This invention provides a method involving competitive binding for identifying a chemical compound which specifically binds to a type 2 ryanodine (RyR2) receptor, which comprises separately contacting cells expressing the RyR2 receptor, or separately contacting a fraction containing sacroplasmic reticulum or endoplasmic reticulum from a cell extract of said cells, with both the chemical compound and a second chemical compound known to bind to the RyR2 receptor, and with only the second chemical compound, under conditions suitable for binding of both compounds, and detecting specific binding of the chemical compound to the RyR2 receptor, a decrease in binding of the second chemical compound to the RyR2 receptor in the presence of the chemical compound indicating that the chemical compound binds to the RyR2 receptor.

In one embodiment of the methods described herein, the chemical compound is not previously known to bind to a type 2 ryanodine (RyR2) receptor.

The invention provides a chemical compound identified by any of the methods described herein.

The invention provides a method of screening a plurality of chemical compounds not known to bind to a type 2 ryanodine (RyR2) receptor to identify a compound which specifically binds to the RyR2 receptor, which comprises:

(a) contacting cells expressing the RyR2 receptor, or contacting a fraction containing sacroplasmic reticulum or endoplasmic reticulum from a cell extract of said cells, with a compound known to bind specifically to the RyR2 receptor;

(b) contacting the cells or fraction of step (a) with the plurality of compounds not known to bind specifically to the RyR2 receptor, under conditions permitting binding of compounds known to bind to the RyR2 receptor;

(c) determining whether the binding of the compound known to bind to the RyR2 receptor is reduced in the presence of the plurality of compounds, relative to the binding of the compound in the absence of the plurality of compounds; and if so (d) separately determining the binding to the RyR2 receptor of each compound included in the plurality of compounds, so as to thereby identify any compound included therein which specifically binds to the RyR2 receptor.

The invention provides a chemical compound identified by any of the methods described herein.

This invention provides a method for determining whether a chemical compound activates a type 2 ryanodine (RyR2) receptor, which comprises contacting cells expressing the RyR2 receptor, or contacting a fraction containing sacroplasmic reticulum or endoplasmic reticulum from a cell extract of said cells, with the chemical compound under conditions suitable for activation of the RyR2 receptor and measuring RyR2 receptor activation in the presence and in the absence of the chemical compound, an increase in RyR2 receptor activation in the presence of the chemical compound indicating that the chemical compound activates the RyR2 receptor. In one embodiment of the method, the chemical compound is not previously known to activate a type 2 ryanodine (RyR2) receptor.

The invention provides a chemical compound identified by any of the methods described herein.

The invention provides a method of screening a plurality of chemical compounds not known to activate a type 2 ryanodine (RyR2) receptor to identify a compound which activates the RyR2 receptor which comprises:

(a) contacting cells expressing the RyR2 receptor, or contacting a fraction containing sacroplasmic reticulum or endoplasmic reticulum from a cell extract of said cells, with the plurality of compounds not known to activate the RyR2 receptor, under conditions permitting activation of the RyR2 receptor;

(b) determining whether the activity of the RyR2 receptor is increased in the presence of one or more of the compounds; and if so (c) separately determining whether the activation of the RyR2 receptor is increased by any compound included in the plurality of compounds, so as to thereby identify each compound which activates the RyR2 receptor.

The invention provides a chemical compound identified by any of the methods described herein.

This invention provides a method for determining whether a chemical compound inhibits activation of a type 2 ryanodine (RyR2) receptor, which comprises separately contacting cells expressing the RyR2 receptor, or separately contacting a fraction containing sacroplasmic reticulum or endoplasmic reticulum from a cell extract of cells, with both the chemical compound and a second chemical compound known to activate the RyR2 receptor, and with only the second chemical compound, under conditions suitable for activation of the RyR2 receptor, and measuring RyR2 receptor activation in the presence of only the second chemical compound and in the presence of both the second chemical compound and the chemical compound, a smaller RyR2 receptor activation in the presence of both the chemical compound and the second chemical compound than in the presence of only the second chemical compound indicating that the chemical compound inhibits activation of the RyR2 receptor. In one embodiment, the chemical compound is not previously known to inhibit activation of a type 2 ryanodine (RyR2) receptor.

The invention provides a chemical compound identified by any of the methods described herein.

This invention provides a method of screening a plurality of chemical compounds not known to inhibit the activation of a type 2 ryanodine (RyR2) receptor to identify a compound which inhibits the activation of the RyR2 receptor, which comprises:

(a) contacting cells expressing the RyR2 receptor, or contacting a fraction containing sacroplasmic reticulum or endoplasmic reticulum from a cell extract of said cells, with the plurality of compounds in the presence of a known RyR2 receptor activator, under conditions permitting activation of the RyR2 receptor;

(b) determining whether the amount of activation of the RyR2 receptor is reduced in the presence of one or more of the compounds, relative to the amount of activation of the RyR2 receptor in the absence of such one or more compounds; and if so (c) separately determining whether each such compound inhibits activation of the RyR2 receptor for each compound included in the plurality of compounds, so as to thereby identify any compound included in such plurality of compounds which inhibits the activation of the RyR2 receptor.

The invention provides a chemical compound identified by any of the methods described herein.

In one embodiment of any of the methods described herein, the RyR2 receptor is a human RyR2 receptor.

In one embodiment of any of the methods described herein, the nucleic acid encoding the RyR2 receptor is endogenous to the cell. In a different embodiment, the nucleic acid encoding the RyR2 receptor is transfected into the cell. In a further embodiment, a beta adrenergic receptor is co-expressed with the RyR2 receptor.

In different embodiments of the above methods, the cell is a bacterial cell, a yeast cell, an insect cell, an amphibian cell or a mammalian cell. In further embodiments, the mammalian cell is a HEK293 cell, a Chinese hamster ovary (CHO) cell, a COS-7 cell, a LM(tk−) cell, a mouse embroyonic fibroblast NIH-3T3 cell, a mouse Y1 cell, a 293 human embryonic kidney cell, or a HeLa cell. In further embodiments, the insect cell is an Sf9 cell, an Sf21 cell or a Trichoplusia ni 5B-4 cell. In further embodiments, the amphibian cell is a *Xenopus oocyte* cell or a *Xenopus melanophore* cell.

In one embodiment of any of the methods described herein, the RyR2 receptor activator is caffeine. In one embodiment, activation of the RyR2 receptor is measured by measuring protein kinase A phosphorylation of the RyR2 receptor. In a further embodiment, protein kinase A phosphorylation of the RyR2 receptor is measured by immunoprecipitating the RyR2 receptor with an anti-RyR2 antibody, back-phosphorylating the RyR2 receptor with protein kinase A and [$\gamma^{32}$P]-ATP, and measuring radioactive $^{32}$P label transferred to the RyR2 receptor. In another embodiment, protein kinase A phosphorylation of the RyR2 receptor is measured using an antibody that is specific for the phosphorylated form of the RyR2 receptor. In a different embodiment, RyR2 receptor activation is measured using a calcium-sensitive fluorescent dye. In further embodiments, the calcium-sensitive fluorescent dye is Fluo-3 or Fura-2.

In one embodiment of the above methods, the cells expressing the RyR2 receptor are cardiac cells from a subject with a failing heart. In different embodiments, the subject is an animal in which heart failure has been induced by rapid cardiac pacing or a human.

In one embodiment of any of the methods described herein, the chemical compound mimics binding of a FKBP12.6 binding protein to the RyR2 receptor. In one embodiment, the chemical compound blocks stimulation of the RyR2 receptor by a catecholamine.

This invention provides a method for making a composition which specifically binds to a RyR2 receptor which comprises identifying a chemical compound using any one of the methods described herein for identifying a chemical compound which specifically binds to a RyR2 receptor, synthesizing the chemical compound or a novel structural and functional analog or homolog thereof, and admixing the chemical compound with a carrier, for example, a pharmaceutically acceptable carrier. The invention also provides a method for making a composition which activates a RyR2 receptor which comprises identifying a chemical compound using any one of the methods described herein for identifying a chemical compound which activates a RyR2 receptor, synthesizing the chemical compound or a novel structural and functional analog or homolog thereof, and admixing the chemical compound with a carrier, for example, a pharmaceutically acceptable carrier. In addition, the invention provides a method for making a composition which inhibits the activation of a RyR2 receptor which comprises identifying a chemical compound using any one of the methods described herein for identifying a chemical compound which inhibits the activation of a RyR2 receptor, synthesizing the chemical compound or a novel structural and functional analog or homolog thereof, and admixing the chemical compound with a carrier, for example, a pharmaceutically acceptable carrier.

This invention provides a method for making a composition of matter which specifically binds to a RyR2 receptor which comprises identifying a chemical compound using any one of the methods described herein for identifying a chemical compound which specifically binds to a RyR2 receptor, and then synthesizing the chemical compound or a novel structural and functional analog or homolog thereof. The invention provides a method for making a composition of matter which activates a RyR2 receptor which comprises identifying a chemical compound using any one of the methods described herein for identifying a chemical compound which activates a RyR2 receptor, and then synthesizing the chemical compound or a novel structural and functional analog or homolog thereof. The invention provides a method for making a composition of matter which inhibits the activation of a RyR2 receptor which comprises identifying a chemical compound using any one of the methods described herein for identifying a chemical compound which inhibits the activation of a RyR2 receptor, and then synthesizing the chemical compound or a novel structural and functional analog or homolog thereof.

This invention provides a pharmaceutical composition comprising (a) an amount of a chemical compound identified using any one of the methods described herein for identifying a compound which activates a RyR2 receptor, or a novel structural and functional homolog or analog thereof, capable of passing through a cell membrane and effective to activate a RyR2 receptor and (b) a pharmaceutically acceptable carrier capable of passing through the cell membrane. The invention provides a pharmaceutical composition comprising (a) an amount of a chemical compound identified using any one of the methods described herein for identifying a compound which inhibits the activation of a RyR2 receptor, or a novel structural and functional homolog or analog thereof, capable of passing through a cell membrane and effective to inhibit the activation of a RyR2 receptor and (b) a pharmaceutically acceptable carrier capable of passing through the cell membrane.

This invention provides a method for preparing a composition which comprises admixing a carrier, for example a pharmaceutically acceptable carrier, and a pharmaceutically effective amount of a chemical compound identified by any of the methods described herein, or a novel structural and functional analog or homolog thereof.

This invention provides a method of treating a subject with a heart disease which comprises administering to the subject a therapeutically effective amount of a chemical compound identified by any of the methods described herein, or a novel structural and functional analog or homolog thereof. In one embodiment, the heart disease is a cardiac failure or a cardiac arrhythmia. In a further embodiment, the cardiac arrhythmia is a ventricular fibrillation or a ventricular tachycardia.

This invention provides the use of a chemical compound, identified using any one of the methods described herein for identifying a compound which activates a RyR2 receptor, for the preparation of a pharmaceutical composition for treating an abnormality, wherein the abnormality is alleviated by activating a RyR2 receptor. The invention provides the use of a chemical compound, identified using any one of the methods described herein for identifying a compound which inhibits the activation of a RyR2 receptor, for the preparation of a pharmaceutical composition for treating an abnormality, wherein the abnormality is alleviated by inhibiting the activation of a RyR2 receptor. In one embodiment, the abnormality is a heart disease. In one embodiment, the heart disease is a cardiac failure or a cardiac arrhythmia. In a further embodiment, the cardiac arrhythmia is a ventricular fibrillation or a ventricular tachycardia.

This invention provides assays for RyR2 receptor channel function which involve measuring protein kinase A (PKA) phosphorylation of the RyR2 receptor, the degree of association of the FKBP12.6 binding protein with the RyR2 receptor, the subconductance state of the RyR2 receptor channel, the $Ca^{2+}$ sensitivity for activation of the RyR2 receptor channel, or the open probability ($P_o$) of the RyR2 receptor channel.

In the subject invention, a "pharmaceutically effective amount" is any amount of a compound which, when administered to a subject suffering from a disease against which the compound is effective, causes reduction, remission, or regression of the disease. Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

Approaches to designing and synthesizing receptor selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

Experimental Details

The following Experimental Details are set forth to aid in an understanding of the invention, and are not intended, and should not be construed, to limit in any way the invention set forth in the claims which follow thereafter.

Materials And Methods

Immunoprecipitation and back-phosphorylation of RyR2. Homogenates and sarcoplasmic reticulum (SR) membranes were prepared from cardiac ventricular tissue as described by Kaftan et al. (1996). Cardiac SR (200 μg) or homogenates (500 μg) were suspended in 0.5 ml of buffer (50 mM Tris-HCl (pH 7.4), 0.9% NaCl, 0.5 mM NaF, 0.5 mM $Na_3VO4$, 0.25% Triton X100, and protease inhibitors). Samples were incubated overnight at 4° C. with the antibodies indicated below (immunoglobulin G (IgG) alone was used as a negative control for immunoprecipitations with each antibody, data not shown). Protein A sepharose beads were added to the samples followed by incubation at 4° C. for 1 hour with constant mixing. Beads were washed with a 1×phosphorylation buffer (8 mM $MgCl_2$, 10 mM ethylene glycol-bis(β-aminoethylether)N,N,N',N'-tetraacetic acid (EGTA), and 50 mM Tris/piperazine-N,N'-bis(2-ethanesulfonic acid), pH 6.8), resuspended in 10 μl of a 1.5×phosphorylation buffer containing either vehicle alone, catalytic subunit of PKA (Sigma, St. Louis, Mo.), or PKA plus a PKA inhibitor ($PKI_{5-24}$, 500 nM, Calbiochem, San Diego, Calif.), or cAMP as indicated. Back-phosphorylation of immunoprecipitated RyR2 was initiated by addition of PKA (5 units) and MgATP (33 μM) and terminated after incubation for 5 minutes at room temperature by the addition of 5μl of stop solution (4% sodium dodecylsulfate (SDS) and 0.25 M dithiothreitol (DTT)). RyR2 phosphorylation with: 1) protein kinase C (PKC) (0.05 units, Calbiochem) was performed under similar conditions (1.5 mM $CaCl_2$ was added to the phosphorylation buffer); and 2) with $Ca^{2+}$/calmodulin-dependent protein kinase (CaMKII, 0.2 μg, Upstate Biotech, Lake Placid, N.Y.); 1.5 mM $CaCl_2$ and 5 μM calmodulin were added to the phosphorylation buffer. In some experiments the adenosine triphosphate (ATP) solution also contained 10% [$\gamma^{32}P$]-ATP (NEN Life Sciences, Boston, Mass.). Samples were heated to 95° C. and size fractionated on 6% SDS-PAGE. The radioactive signal corresponding to the RyR2 band was quantified using a Molecular Dynamics Phosphorimager and ImageQuant software (Amersham Pharmacia Biotech, Piscataway, N.J.). Back-phosphorylation was quantified using a phosphorimager, non-specific phosphorylation (not inhibited by addition of the PKA inhibitor) was subtracted and the resulting value was divided by the amount of RyR2 protein in each immunoprecipitate (determined by immunoblotting and densitometry or by [$^3$H] ryanodine binding) and expressed as the inverse of the PKA-dependent [$\gamma^{32}$P]-ATP signal. Microcystin-sepharose (35 µl, UBI) was used to isolate RyR2 from 200 µg of cardiac SR by incubating at 4° C. for 1 hour followed by washing. Beads were resuspended in 6×SDS loading buffer, boiled and the supernatant was size fractionated on SDS-PAGE. Phosphatases PP1 and PP2A bound to the microcystin-sepharose beads were competed off with addition of free microcystin-LR (Calbiochem).

Stoichiometry of PKA Phosphorylation. Maximum PKA-dependent phosphorylation was determined by pre-treatment of RyR2 with alkaline phosphatase (AP, 1:100 enzyme:protein, New England Biolabs) for 20 minutes at 37° C. to remove bound phosphate. The reaction was terminated by the addition of 5 µl of stop solution. NaF was omitted, then added after dephosphorylation to terminate the reaction. Samples were back-phosphorylated with PKA as described above. To calculate the stoichiometry of PKA phosphorylation of RyR2 a phosphorimager was used to calibrate signals generated by [$\gamma^{32}$P] -ATP standards of known specific activity (from $2.0 \times 10^{-4}$ to $2.0 \times 10^{-3}$ µCi/µL). The molar ratio of $^{32}$P/RyR2 was calculated by dividing the $^{32}$P-phosphorylation by the amount of high affinity [$^3$H] ryanodine binding (one high affinity ryanodine binding site per RyR2) in each sample of immunoprecipitated RyR2 protein.

Immunoblots. Immunoblots were performed as described (Moschella and Marks, 1993) using the following antibodies: anti-FKBP12 (1:1000), anti-RyR (5029, 1:3000) (Jayaraman et al., 1992), anti-PP1 (1:1000), anti-PP2A (1:1000), anti-CnA (1:1000), anti-PKA catalytic subunit (1:1000, Transduction Labs, Lexington, Ky.), anti-phosphoserine (1 µg/ml, Zymed San Francisco, Calif.), anti-mAKAP (3 µg/ml, Upstate Biotechnology, Lake Placid, N.Y.), or purified VO56 (anti-mAKAP antibody) (Kapiloff et al., 1999). After washing, membranes were incubated with peroxidase conjugated goat anti-rabbit or goat anti-mouse IgG antiserum (1:3000, Boehringer-Mannheim) for 60 minutes at room temperature, washed X3 with tris buffered saline (TBS), 0.1% Tween 20, and developed using enhanced chemiluminescence (ECL, Amersham).

Yeast two-hybrid assay to identify the FKBP12.6 binding site. Human FKBP12.6 cDNA was subcloned into the yeast two hybrid vector pEG202 (OriGene Technologies, Rockville, Md.) to make pEGFKBP12.6 (FKBP12.6 fused to the GAL4 DNA binding domain). Human RyR2 cDNA fragments subcloned into the yeast two hybrid vector pJG4-5 (OriGene) were confirmed by sequencing. The yeast two hybrid assay for protein-protein interaction was performed using the DupLEX-A yeast system (OriGene) per manufacturer's instructions. pEGFKBP12.6 and pAD-GAL4RyR2/2361-2496 were co-transformed into the rapamycin resistant mutant yeast strain Y663 (Lorenz and Heitman, 1995), and liquid β-galactosidase assays were performed in the absence or presence of rapamycin (0.1,1.0, and 10 µM) which competes with RyR2 for binding to FKBP12.6.

Site-directed mutagenesis, expression of GST-RyR2 fusion proteins and in vitro mapping. pGST-RyR2 constructs were generated using rabbit or human RyR2 cDNA, and fusion proteins were expressed and purified with glutathione sepharose beads. Site-directed mutagenesis was performed using the 5' Prime-3'-Prime Site-directed Mutagenesis Kit (Amersham Pharmacia Biotech) as per manufacturer's instructions. pGST-RyR2 fusion proteins bound to sepharose beads were incubated with canine cardiac SR (200 µg), pelleted, washed with modified RIPA buffer, size fractionated on SDS-PAGE, and immunoblotted with the indicated antibodies.

Immunohistochemistry. Human cardiac tissue was fixed in 10% neutral buffered formalin, and embedded in paraffin. Sections (4 µM) were dried overnight at 37° C., de-waxed with xylenes, re-hydrated, incubated with phosphate buffered saline (PBS)+0.2% Tween-20 for 5 minutes, then incubated with 5% goat serum in PBS for 1 hour at room temperature. Sections were then incubated with either pre-immune rabbit serum (IgG) or primary antibody [mAKAP (V056), RyR2 (monoclonal, Affinity Bioreagents); 1:50] in PBS+3% bovine serum albumin (BSA) overnight at 4° C., followed by intensive washing with PBS. Sections were then incubated with either FITC or rhodamine secondary antibody (1:100; Zymed) in 3% BSA-PSA for 1 hour at room temperature, washed with PBS and stained with Hoescht dye (10 µg/ml) for 5 minutes, followed by intensive PBS washing. For double immunostaining, slides were sequentially stained with two individual primary antibodies followed by simultaneous incubation with the secondary antibodies. Immunostained slides were examined using a Nikon microscope with 100×objective; images were acquired with a SPOT RT camera (Diagnostic Instruments Inc) using Adobe Photoshop.

Isolation of RyR2 and single channel recordings. Cardiac muscle heavy SR was incubated with [$^3$H]ryanodine, solubilized with 3-[(3-Cholamidopropyl)-dimethylammonio]-1-propanesulfonate (CHAPS) and centrifuged for 14 hours on a 10 to 32% linear sucrose gradient at 26,000 rpm, 2° C. in a Sorvall AH-629 rotor (Brillantes et al., 1994; Marx et al., 1998). Single channel recordings were performed as described (Brillantes et al., 1994). Single channel properties were evaluated using pCLAMP 6.02 software (Axon Instruments). Open probabilities were determined by analyzing data at 10 and 30 second intervals over a minimum of 3 minutes. At the conclusion of each experiment ryanodine and/or ruthenium red were applied to confirm the identity of channels as ryanodine receptors. Results are presented as mean±standard deviation. The Student's t-test was used for statistical analyses of the dwell time distributions and open probabilities.

Human heart samples and left ventricular assist device (LVAD). The use of human tissues for this study was approved by the Institutional Review Board of Columbia-Presbyterian Medical Center. Normal and failing human heart tissues were obtained as previously described from patients undergoing cardiac transplant (Go et al., 1995). Left ventricular assist devices (Thermo Cardiosystems Inc., Woburn, Mass.) were implanted in patients as a bridge to heart transplantation according to standard clinical practice (Frazier, 1994).

Muscle strip function. Trabeculae (diameters<1 mm, lengths>3 mm) were obtained from human left ventricular apical core samples obtained at the time of LVAD implantation or from hearts explanted at the time of orthotopic cardiac transplantation. Trabeculae were placed in a standard muscle bath, attached to a force transducer and stimulated at 1 Hz, left to equilibrate for 1 hour prior to study at slack length, then stretched progressively to the point of maximal tension development ($L_{max}$). β-adrenergic response was tested by superfusing the muscle with Krebs-Ringer solution containing isoproterenol (4 µM).

Canine heart failure model. Canine heart failure was induced by rapid cardiac pacing at 210 beats/minute for 3 weeks followed by an additional week of pacing at 240 beats/minute as described previously (Wang et al., 1997). This rapid cardiac pacing regimen induces severe heart failure as evidenced by an average 40% reduction in left ventricular $dP/dt_{max}$ (to ~1800 mmHg/second), 20% reductions in peak left ventricular and mean aortic pressures (to 100 and 85 mm Hg, respectively), a 50% increase in resting heart rate (to 132 beats/minute), and a rise in end-diastolic pressure to greater than 20 mm Hg (Wang et al., 1997). All procedures were approved by the Institutional Animal Care Committee.

Methods of transfecting cells. Methods of transfecting cells with nucleic acid encoding a ryanodine receptor to obtain cells in which the ryanodine receptor is expressed are known in the art (see, for example, Brillantes et al., 1994). In non-muscle cells, the RyR2 receptor is expressed on the endoplasmic reticulum. The cells may be additionally transfected with nucleic acid encoding a beta adrenergic receptor to obtain cells in which both the RyR2 receptor and beta adrenergic receptor are expressed. Such transfected cells may also be used to test compounds and screen compound libraries to obtain compounds which bind receptors as well as compounds which activate or inhibit activation of functional responses in such cells, and therefore are likely to do so in vivo.

A broad variety of host cells can be used to study heterologously expressed proteins. These cells include but are not limited to mammalian cell lines such as, for example, Cos-7, Chinese hamster ovary (CHO), LM(tk−), HEK293; insect cell lines such as, for example, Sf9, Sf21; amphibian cells such as *Xenopus oocytes*; assorted yeast strains; assorted bacterial cell strains; and others. Culture conditions for each of these cell types is specific and is known to those familiar with the art.

DNA encoding proteins to be studied can be transiently expressed in a variety of mammalian, insect, amphibian, yeast, bacterial and other cells lines by several transfection methods including but not limited to: calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin.

Binding assays. Methods of conducting binding assays are well known in the art. Labeled compounds are placed in contact with intact cells, or a cell extract containing sacroplasmic reticulum or endoplasmic reticulum, expressing the RyR2 receptor. Methods of preparing a cell extract containing sacroplasmic reticulum or endoplasmic reticulum are know in the art (e.g., Kaftan et al., 1996). If the compound is labeled with a radioactive isotope such as $^3H$, $^{14}C$, $^{125}I$, $^{35}S$, $^{32}P$, $^{33}P$, the bound compound may be detected by using liquid scintillation counting, scintillation proximity, or any other method of detection for radioactive isotopes. If the compound was labeled with a fluorescent compound, the bound labeled compound may be measured by methods such as, but not restricted to, fluorescence intensity, time resolved fluorescence, fluorescence polarization, fluorescence transfer, or fluorescence correlation spectroscopy. In this manner, compounds that bind to the receptor may be identified as they inhibit the binding of the labeled compound to the receptor.

Assays for compounds to treat heart disease. PKA phosphorylation of RyR2 increases the activity of the RyR2 channel resulting in the release of more calcium into the cytoplasm of the cell for a given activator of the channel. Compounds that block PKA activation of RyR2 would be expected to reduce the activation of the RyR2 channel resulting in less release of calcium into the cell. Compounds that bind to the RyR2 channel at the FKBP12.6 binding site but do not come off the channel when the channel is phosphorylated by PKA would also be expected to decrease the activity of the channel in response to PKA activation or other triggers that activate the RyR2 channel. Such compounds would also result in less calcium release into the cell.

One assay for compounds that may be effective in treating heart disease involves measuring the release of calcium into cells via the RyR2 channel using calcium-sensitive fluorescent dyes (e.g. Fluo-3, Fura-2). The assay involves loading cells with the fluorescent dye and stimulating the cells with a RyR2 activator and determining whether or not a compound added to the cells reduces the calcium-dependent fluorescent signal (Brillantes et al., 1994; Gillo et al, 1993; Jayaraman et al., 1996). One RyR2 activator is caffeine which can be added to the cell. When calcium is released into the cytoplasm of the cell it is bound by the calcium-sensitive dye which then emits a fluorescent signal. Calcium-dependent fluorescent signals are monitored with a photomultiplier tube and analyzed with appropriate software as described by Brillantes et al., 1994; Gillo et al, 1993; and Jayaraman et al., 1996. This assay can be easily automated to screen large numbers of compounds using multiwell dishes. The assay involves expressing recombinant RyR2 channels in a heterlogous expression system such as bacterial, yeast, insect, Sf9, HEK293, CHO, COS-7, LM(tk−), mouse embroyonic fibroblast NIH-3T3, 293 human embryonic kidney, or HeLa cells (Brillantes et al., 1994). In non-muscle cells, the RyR2 receptor is expressed on the endoplasmic reticulum. When the RyR2 channel is activated, calcium is released from the endoplasmic reticulum into the cytoplasm of the cell. RyR2 receptors could be co-expressed with beta adrenergic receptors. This would permit the assessment of compounds on RyR2 receptor activation in response to addition of beta adrenergic receptor agonists.

Another assay involves measuring the level of protein kinase A phosphorylation of RyR2 which correlates with the degree of heart failure and can be used to determine the efficacy of compounds designed to block the protein kinase A phosphorylation of the RyR2 channel. This assay can be used in connection with animal models in which heart failure is induced by rapid cardiac pacing. The assay is based on the use of antibodies that are specific for the RyR2 channel protein (anti-RyR2 antibody). For this assay the RyR2 channel protein is immunoprecipitated with the anti-RyR2 antibody and then back-phosphorylated with protein kinase A and [$\gamma^{32}P$]-adenosine triphosphate (ATP). The amount of radioactive $^{32}p$ label that is transferred to the RyR2 receptor protein can be measured using a phosphorimager. In another version of the assay, the antibody is specific for the phosphorylated form of the RyR2 receptor, in which case back-phosphorylation is not necessary.

Other assays for RyR2 receptor channel function involve measuring the degree of association of the FKBP12.6 binding protein with the RyR2 receptor, the subconductance state of the RyR2 receptor channel, the $Ca^{2+}$ sensitivity for activation of the RyR2 receptor channel, or the open probability ($P_o$) of the RyR2 receptor channel.

Results

Protein Kinase A Phosphorylates RyR2. The 565,000 dalton RyR2 polypeptide was PKA phosphorylated in in vitro kinasing reactions (FIG. 1A). To confirm the identity of the PKA phosphorylated high molecular weight protein as RyR2 the phosphorylated band was immunoblotted with anti-RyR antibody. The specificity of the phosphorylation was demonstrated using a PKA inhibitor (FIG. 1A). Addition of phosphorylation buffer including cAMP without exogenous PKA also resulted in phosphorylation of RyR2 that was inhibited by PKI indicating that endogenous PKA was associated with RyR2 (FIG. 1A). The stoichiometry of PKA phosphorylation was determined by immunoprecipitating RyR2 from cardiac muscle SR, fully dephosphorylating the RyR2 protein with alkaline phosphatase, and then phosphorylating with PKA and $[\gamma^{32}P]$-ATP. The stoichiometry of PKA phosphorylation was 3.8±0.1 moles of phosphate per mole of channel (each channel comprises four RyR2 subunits) or about one mole of phosphate per RyR2 subunit indicating that each RyR2 protein is PKA phosphorylated on a single amino acid residue.

Figure 1B:
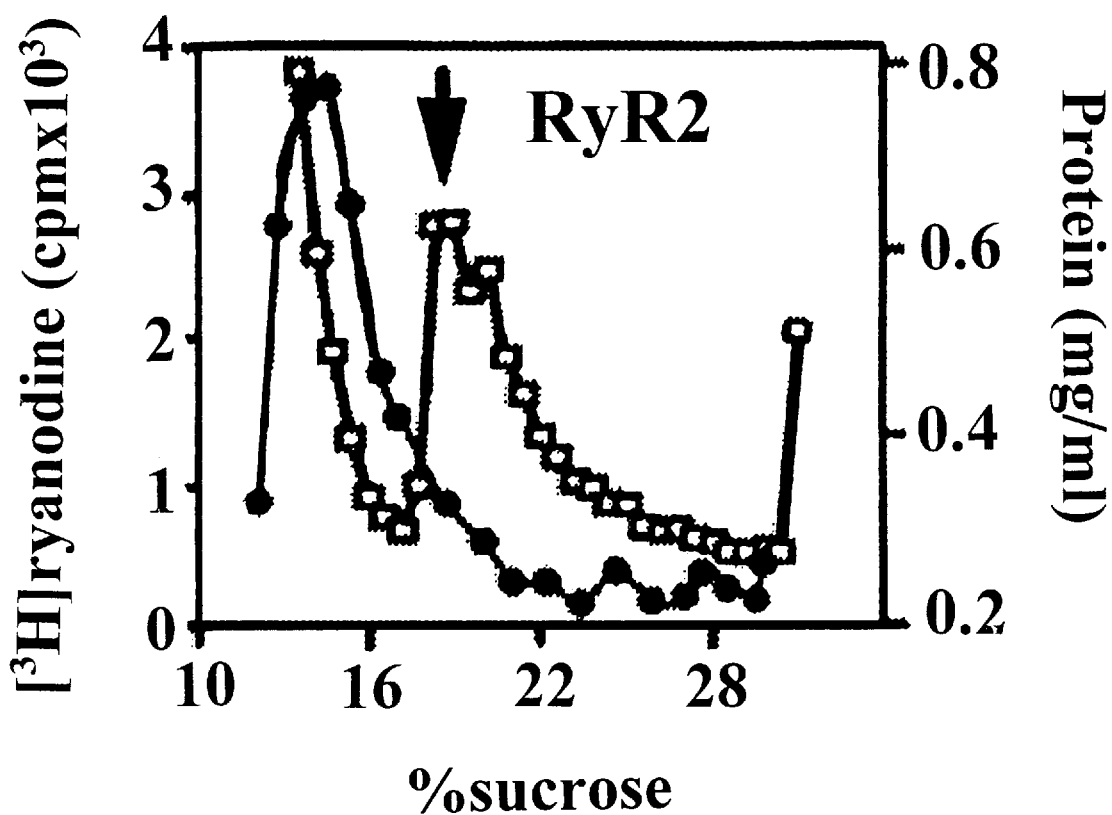
Figure 1C:
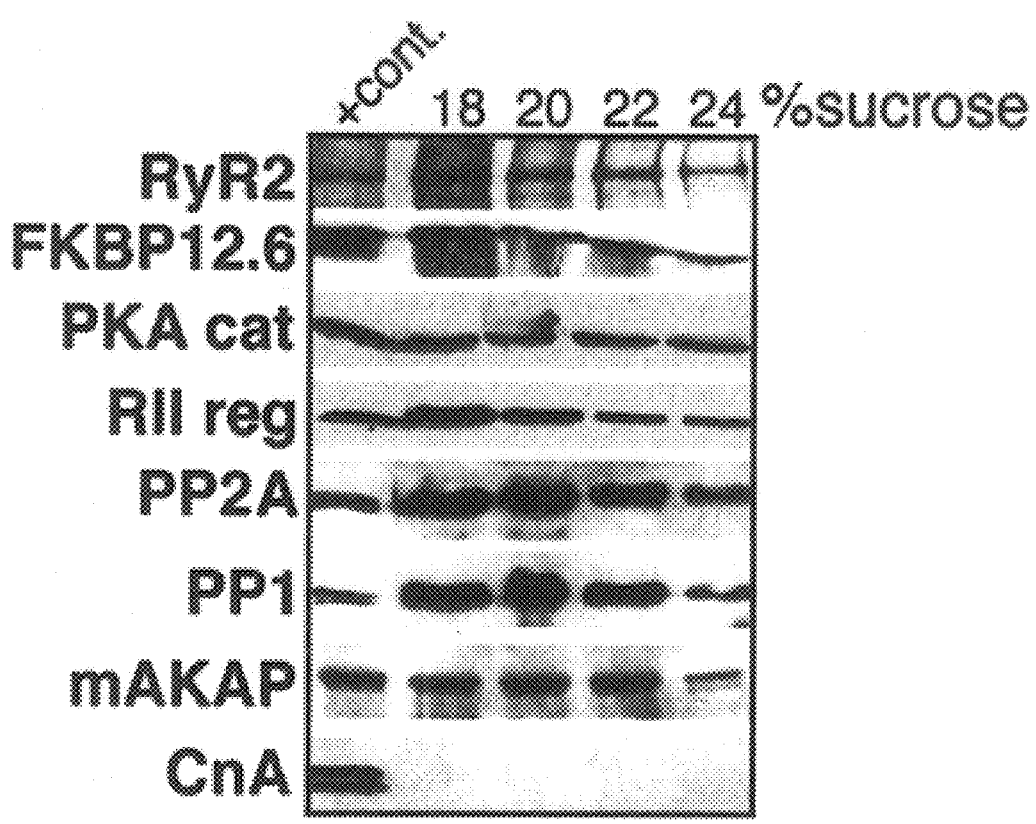

RyR2 Macromolecular Complex Includes FKBP12.6, PKA, PP1, PP2A and mAKAP. RyR2 was isolated by sucrose density gradient centrifugation using [$^3$H] ryanodine (FIG. 1B) as described (Marx et al., 1998). Individual tetrameric RyR2 channels sediment as 30S complexes and multiple channels (two or more) sediment as denser complexes (Marx et al., 1998). The muscle A kinase anchoring protein (mAKAP) that binds PKA and targets it to substrates has been localized to cardiac SR (Kapiloff et al., 1999; Yang et al., 1998). The major protein phosphatases in cardiac muscle are protein phosphatase 2A (PP2A), protein phosphatase 1 (PP1) (MacDougall et al., 1991), and calcineurin (CnA). Fractions from the sucrose gradient were immunoblotted with either anti-RyR antibody or with antibodies that recognize FKBP12.6, the catalytic subunit of PKA, the PKA regulatory subunit (RII), PP2A, PP1, mAKAP or CnA (FIG. 1C) all of which (with the exception of CnA) were detected in all fractions containing RyR2. These data are consistent with a high molecular weight complex comprised of RyR2, FKBP12.6, PKA, RII, PP1, PP2A and mAKAP.

Figure 1D:
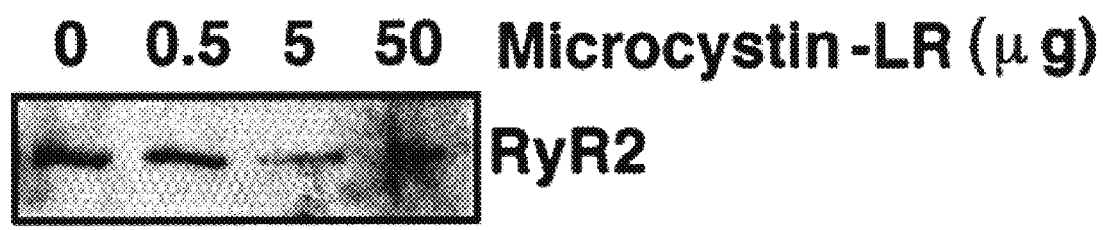
Figure 1E:
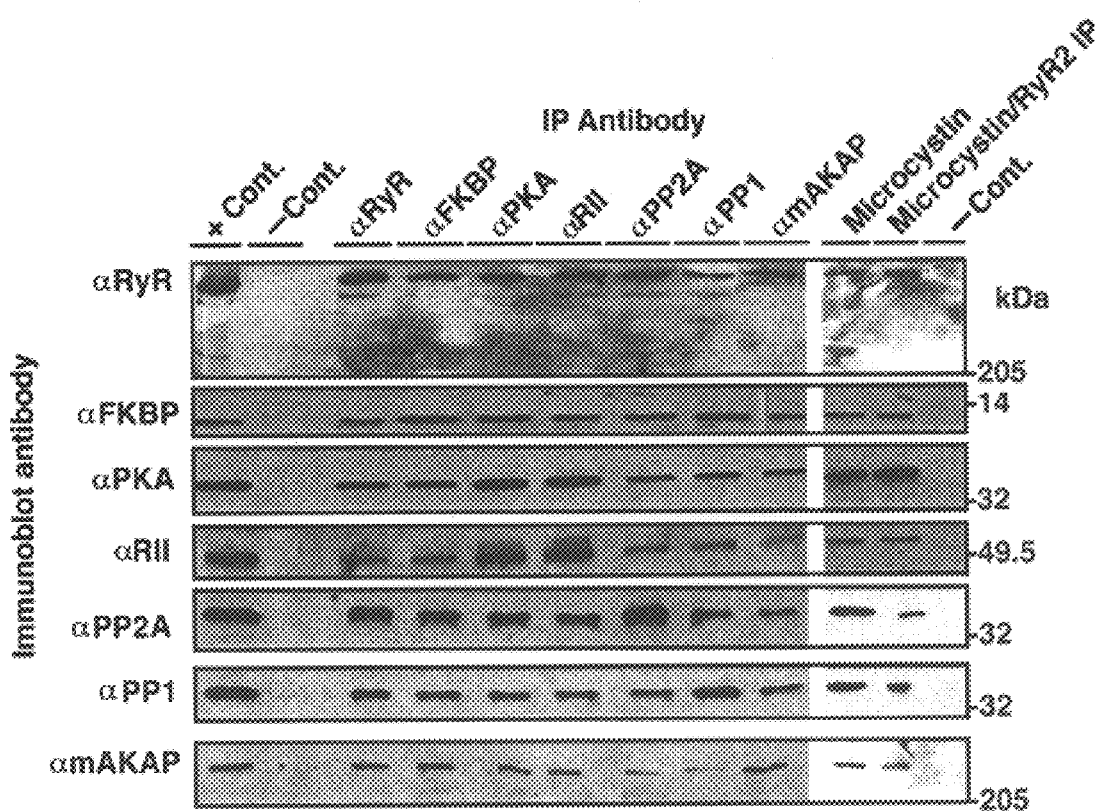

The phosphatase inhibitor microcystin binds to PP1 and PP2A. RyR2 was sedimented by binding to microcystin-sepharose beads, and the specificity of this interaction was demonstrated by competing off RyR2 using free microcystin-LR (FIG. 1D). Co-immunoprecipitations were performed showing that FKBP12.6, PKA, RII, PP2A, PP1 and mAKAP all co-immunoprecipitated with RyR2, indicating physical association of these proteins and the SR $Ca^{2+}$ release channel (FIG. 1E). The existence of a macromolecular complex was shown independently by first sedimenting the complex with microcystin-sepharose beads followed by competing the complex off from the beads with free microcystin-LR and then immunoprecipitating each of the components of the complex (FIG. 1E, last three lanes). Taken together these data show that FKBP12.6, PKA, RII, PP1, PP2A and mAKAP comprise a macromolecular complex with RyR2.

PKA Hyperphosphorylation of RyR2 in Failing Heart Muscle. Increased sympathetic activity is an important physiologic response to stress resulting in activation of the adrenergic signaling pathway that generates increased cAMP levels and activates PKA. In failing hearts (regardless of the etiology of the damage to the heart) circulating catecholamine levels are markedly increased. Specific PKA phosphorylation of RyR2 in normal and failing hearts was examined using both back phosphorylation with $[\gamma^{32}P]$-ATP and anti-phosphoserine immunoblots (FIGS. 2A and 2B).

Figure 2A:
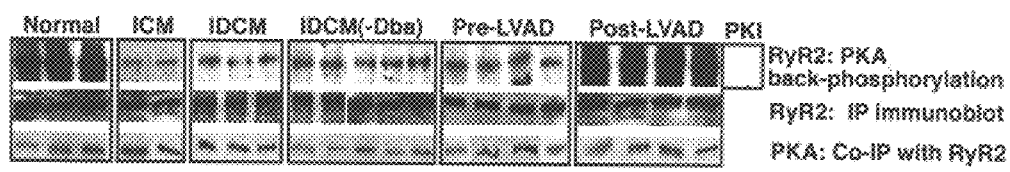
Figure 2B:
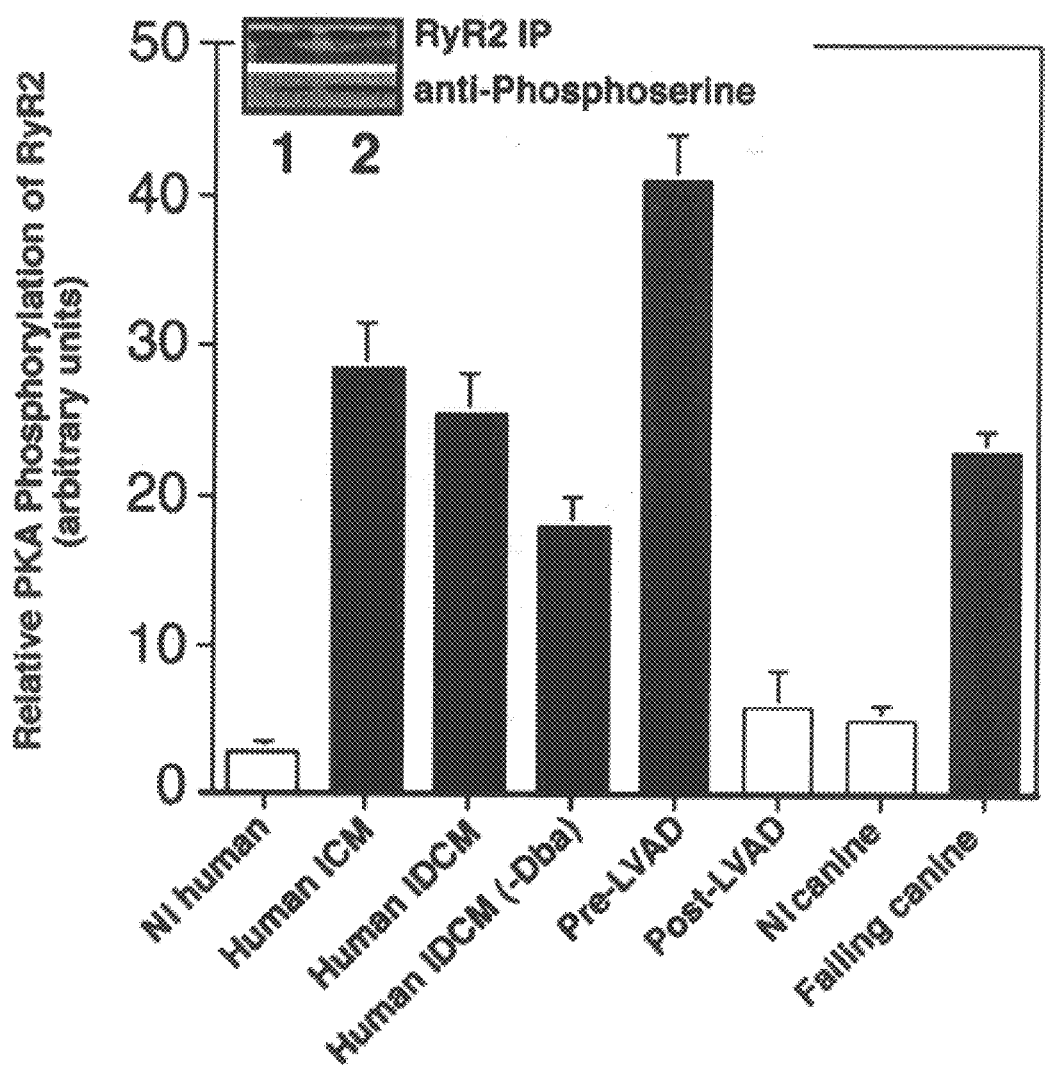

Strikingly, PKA phosphorylation of RyR2 was significantly elevated in failing hearts from humans and from animal models (dogs with pacing-induced heart failure) compared to non-failing hearts (FIGS. 2A and 2B). PKA phosphorylation of RyR2 channels from failing hearts was increased ~4-fold compared to RyR2 channels from non-failing hearts. The stoichiometry of PKA back-phosphorylation of RyR2 channels isolated from failing hearts was 0.7±0.3 moles of phosphate transferred per mole of channel (n=8) compared to 3.1±0.1 moles of phosphate transferred per mole of channels from normal non-failing hearts, (n=6, p<0.0001). These data suggest that in failing hearts approximately three of the four PKA sites on the tetrameric RyR2 channel are phosphorylated in vivo, whereas only one site is phosphorylated in vivo on RyR2 isolated from normal non-failing hearts.

This increase in PKA phosphorylation of RyR2 was not due to an increase in the levels of PKA protein associated with RyR2 in failing hearts as determined by co-immunoprecipitation of PKA with RyR2 (FIG. 2A). PKA back-phosphorylation was performed using immunoprecipitated RyR2 to ensure that the phosphorylation signal which was measured represented specifically RyR2 PKA phosphorylation. RyR2 levels are decreased in failing hearts (Go et al., 1995). PKA phosphorylation of RyR2 was normalized to the amount of immunoprecipitated RyR2 protein to enable valid comparisons of the amount of PKA phosphorylation per RyR2 molecule from normal and failing hearts (FIGS. 2A and 2B). Moreover, identical results were obtained when immunoprecipitated RyR2 was immunoblotted with an anti-phosphoserine antibody (e.g. see FIG. 2B inset) confirming that the RyR2 channels from failing hearts were PKA hyperphosphorylated compared to channels from non-failing hearts.

Left ventricular assist devices (LVADs) are used as a bridge to transplantation when donor hearts are not available. Studies have shown that the hemodynamic unloading of the left ventricle provided by LVADs results in a significant improvement in cardiac contractile function when the device is implanted in failing hearts (Levin et al., 1995). At the time of LVAD insertion a tissue core is removed from the patient's left ventricle and this tissue can then be compared to tissue from the explanted heart which becomes available at the time of transplantation. Thus, the pre-LVAD sample comes from failing hearts and the post-LVAD sample comes from hearts with improved function. PKA phosphorylation of RyR2 was significantly increased in pre-LVAD heart samples compared to samples from non-failing hearts and returned to normal levels following LVAD treatment (FIGS. 2A and 2B). Taken together these data show: 1) PKA phosphorylation of RyR2 is regulated physiologically in vivo; 2) heart failure is associated with increased PKA phosphorylation of RyR2; and 3) the PKA phosphorylation of RyR2 returns to normal levels when the cardiac function is improved by LVAD insertion.

Many patients with end-stage heart failure are treated with β-adrenergic agonists (e.g. dobutamine) prior to cardiac transplantation, while some patients are admitted directly from home when a donor heart becomes available and therefore are not receiving β-adrenergic agonists which are administered intravenously in the hospital. PKA phosphorylation of RyR2 was significantly elevated in the hearts from patients not on β-adrenergic agonists compared to normals (FIGS. 2A and 2B). PKA phosphorylation of RyR2 was significantly further increased in hearts from those patients treated with β-adrenergic agonists prior to cardiac transplantation (FIGS. 2A and 2B). These data indicate that exogenous administration of β-adrenergic agonists to patients with heart failure can further increase the PKA phosphorylation of RyR2 in the heart.

Figure 2C:
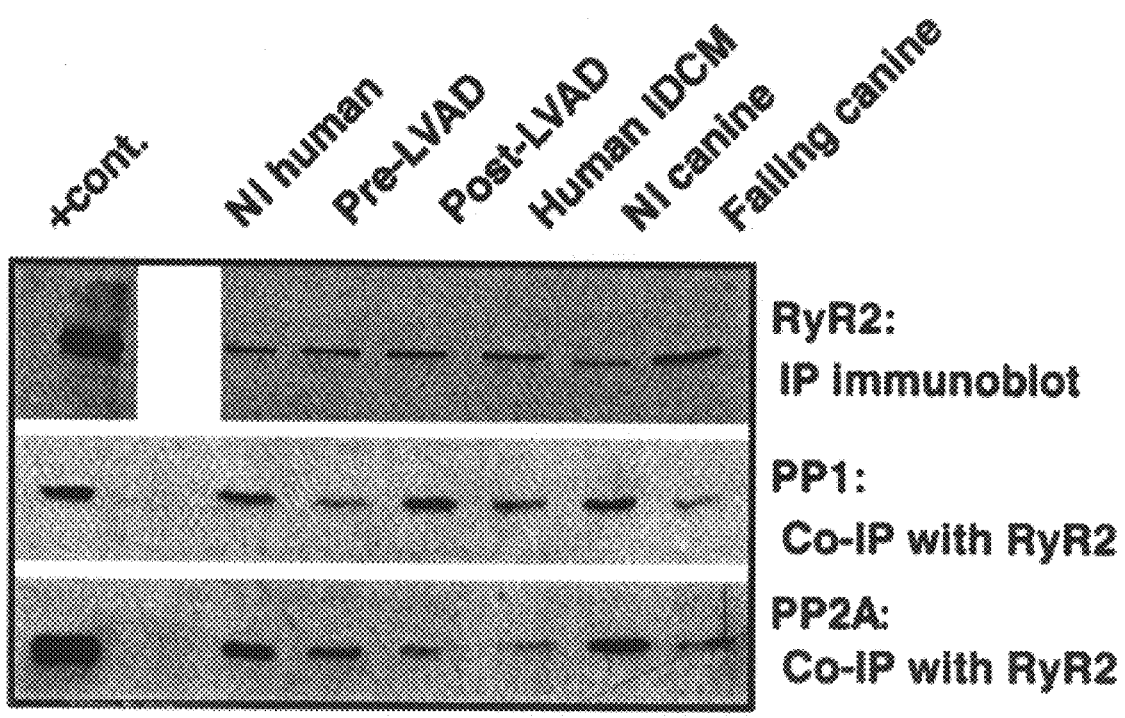

To determine whether the increased PKA phosphorylation of RyR2 observed in failing hearts was explained solely by an increase in PKA activity or possibly by a concomitant decrease in the activity of phosphatases which catalyze the removal of phosphate groups, the amounts of PP1 and PP2A physically associated with RyR2 in failing hearts were compared to those in normal hearts from humans and dogs (FIGS. 2C and 2D). There was a significant decrease in the levels of PP1 and PP2A that co-immunoprecipitated with RyR2 from failing hearts (FIGS. 2C and 2D). The decrease in the amount of PP1 (but not of PP2A) associated with RyR2 was restored to normal by LVAD treatment (FIGS. 2C and 2D). These data suggest that at least in part the PKA hyperphosphorylation of RyR2 is due to a decrease in phosphatase bound to the RyR2 channel macromolecular complex.

Figure 3A:
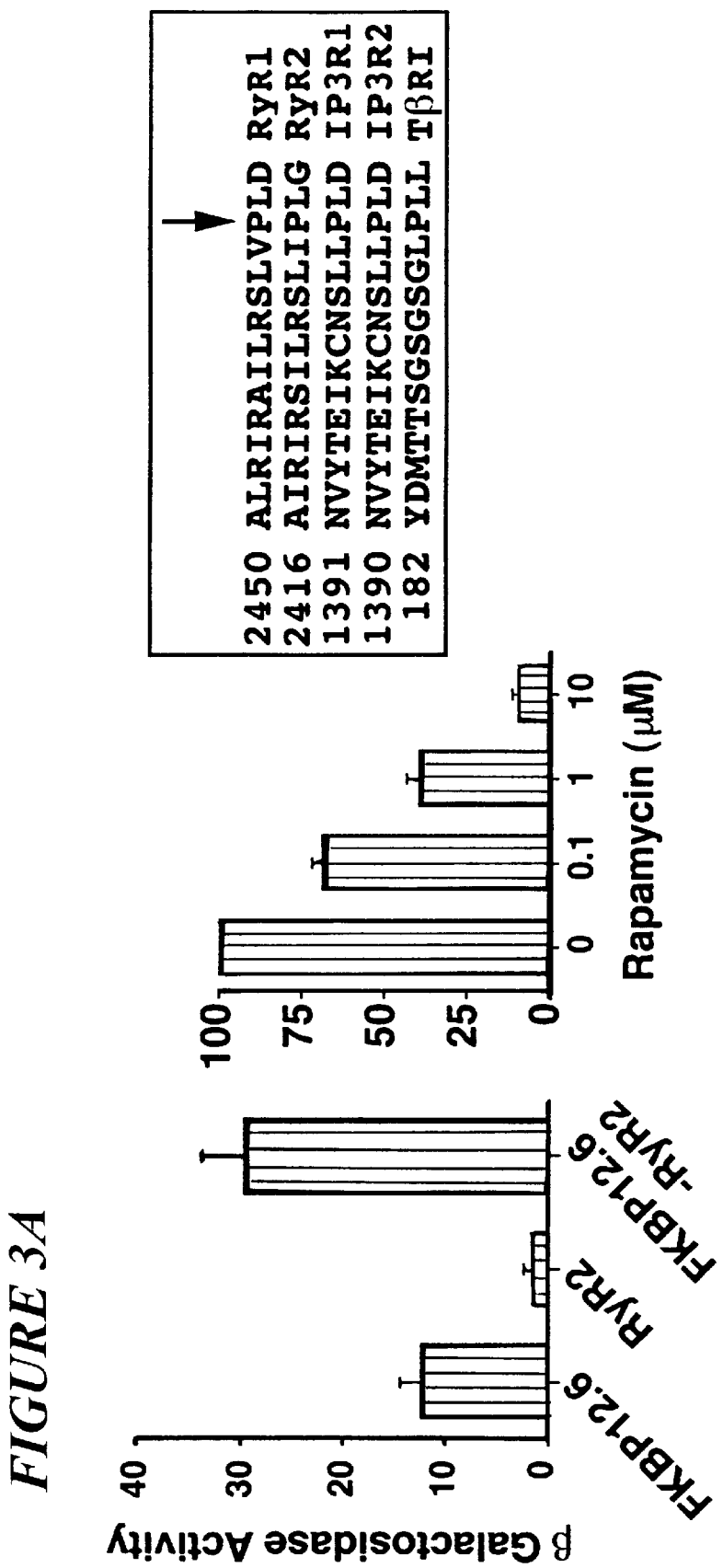
Figure 3B:
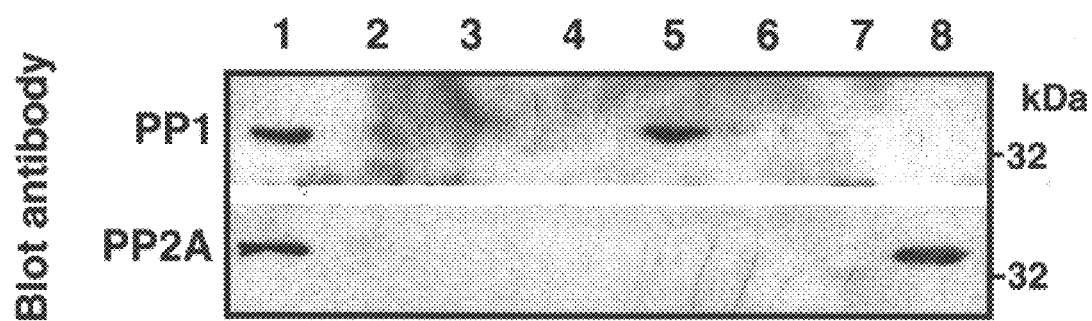
Figure 3C:
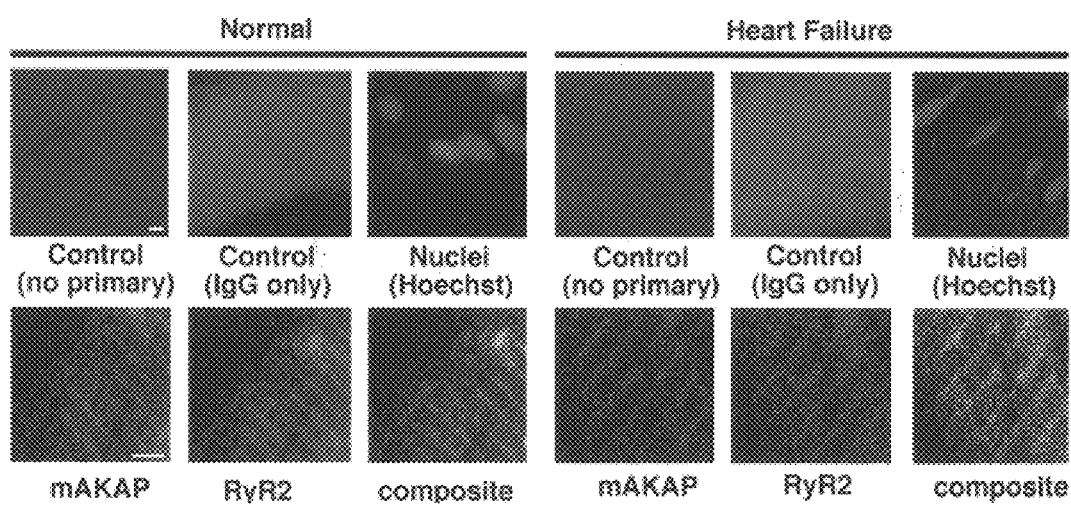
Figure 3D:
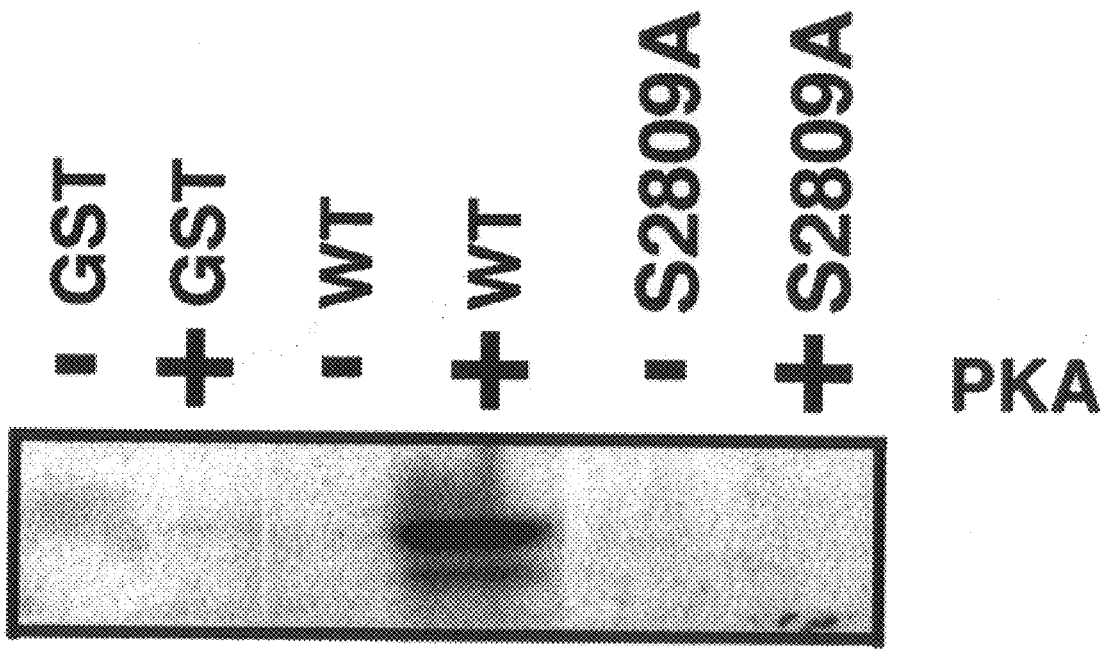

Mapping Signaling Complex Binding Sites on RyR2. The FKBP12.6 binding site on RyR2 was identified using a yeast two-hybrid protein interaction screen in which yeast were transformed with vectors containing either fragments of RyR2 or the full length FKBP12.6 fused to the Gal4 activation domain or DNA binding domain. One RyR2 fragment corresponding to amino acid residues 2361–2496 (Otsu et al., 1990) resulted in a positive interaction with FKBP12.6 as determined by an increase in β-galactosidase activity (FIG. 3A) Using rapamycin-resistant yeast (Lorenz and Heitman, 1995), rapamycin was shown to specifically inhibit the interaction between FKBP12.6 and RyR2 (FIG. 3A) in yeast in a concentration-dependent manner indicating that the interaction between FKBP12.6 and RyR2 was specific. This fragment contains the hydrophobic motif comprised of isoleucine 2427 and proline 2428 (FIG. 3A) that is homologous to the FKBP12 binding site in RyR1, IP3R1 (Cameron et al., 1997), and TRI (FIG. 3A). Using GST-RyR2 fusion proteins in pull-down assays with cardiac SR, binding domains on RyR2 for PP1 (residues 513–808), and PP2A (residues 1451–1768) were mapped (FIG. 3B). Interestingly, the binding domains for PP1 and PP2A both contain leucine/isoleucine zippers. Immunohistochemistry showed that mAKAP is present in the cardiac SR, the same cellular location as RyR2, and there was no difference in this regard between normal and failing human hearts (FIG. 3C). Wild type and mutant GST-RyR2 fusion proteins were used to determine the site of PKA phosphorylation (serine 2809, FIG. 3D).

Figure 4A:
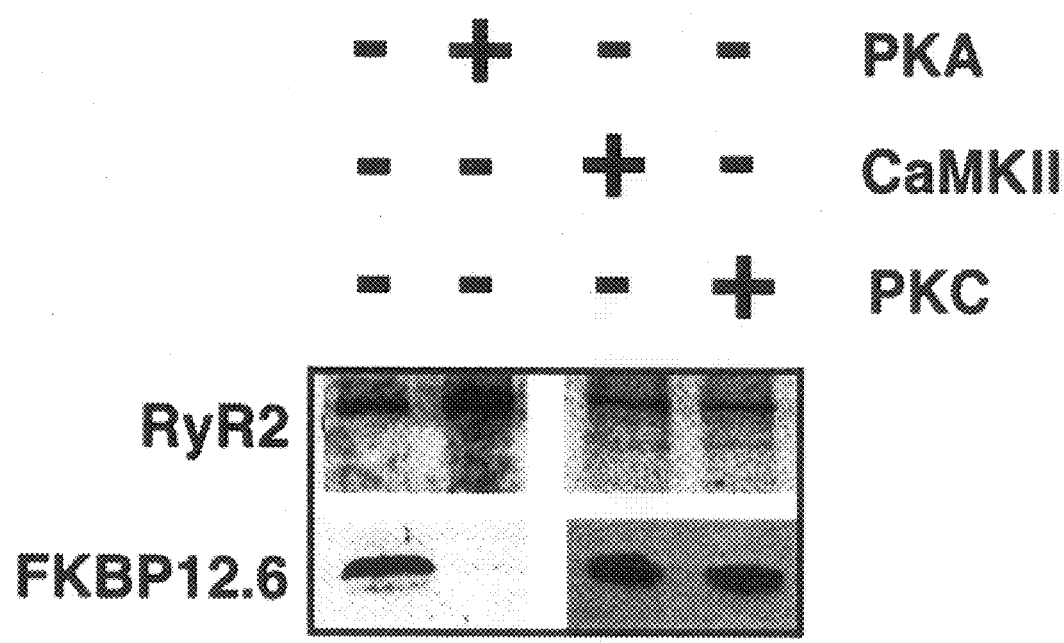
Figure 4B:
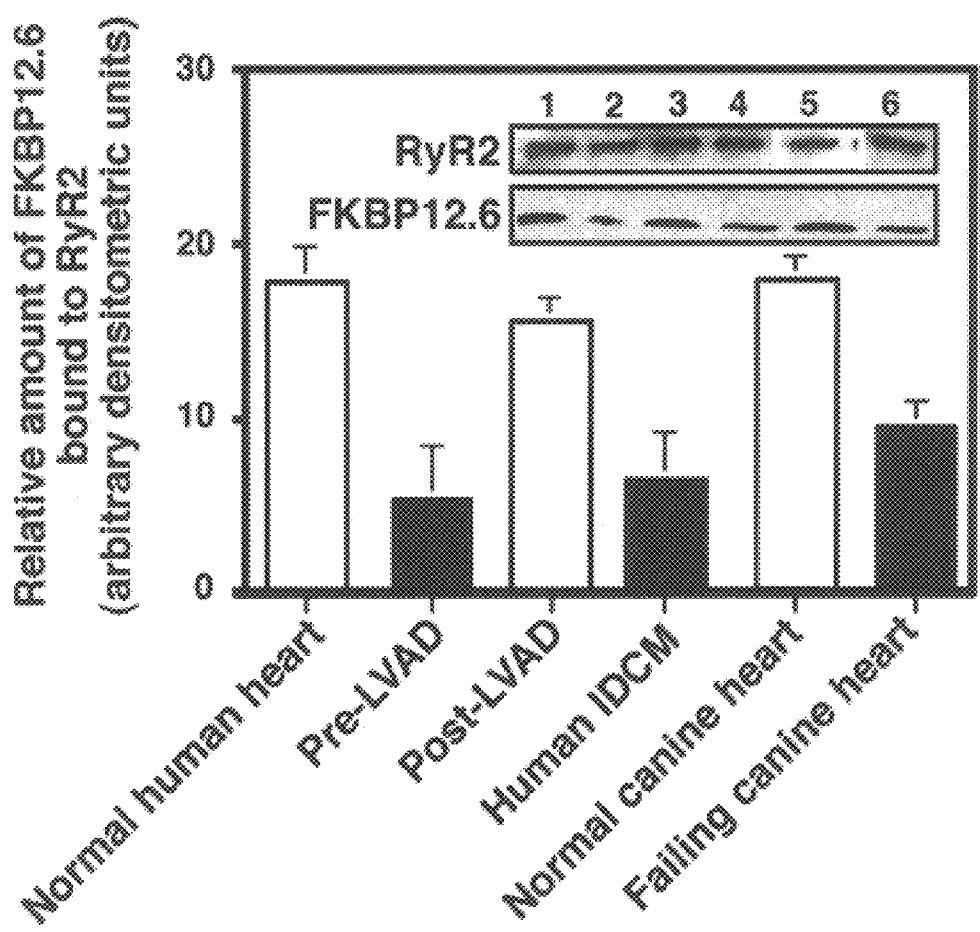

PKA Phosphorylation of RyR2 Inhibits FKBP12.6 Binding. PKA phosphorylation of immunoprecipitated RyR2 (there was no PKA phosphorylation of FKBP12.6) resulted in a significant decrease (~90±9% reduction, n=8, p<0.001) in the amount of FKBP12.6 co-immunoprecipitating with RyR2 (FIG. 4A). No dissociation of FKBP12.6 from RyR2 was observed in the following negative controls: 1) including the PKA inhibitor PKI in the reaction; 2) boiling the PKA; 3) omitting ATP. Neither $Ca^{2+}$ calmodulin kinase (CaMKII) nor protein kinase C (PKC), both of which phosphorylate RyR2, caused the dissociation of FKBP12.6 from RyR2 indicating that the PKA phosphorylation-induced dissociation of FKBP12.6 from RyR2 is a specific effect (FIG. 4A). Furthermore, there was a significant decrease in the amount of FKBP12.6 that co-immunoprecipitated with RyR2 from failing hearts compared to normal hearts both in humans (65±11% reduction, n=4, p<0.005) and in dogs with pacing-induced heart failure (50±8% reduction, n=3, p<0.005) (FIG. 4B). The total amount of FKBP12.6 was the same in homogenates from normal and failing hearts as determined by immunoblotting (data not shown). These data show that PKA phosphorylation of RyR2 provides a mechanism for the physiologic and pathophysiologic regulation of FKBP12.6 binding to RyR2.

Figure 5A:
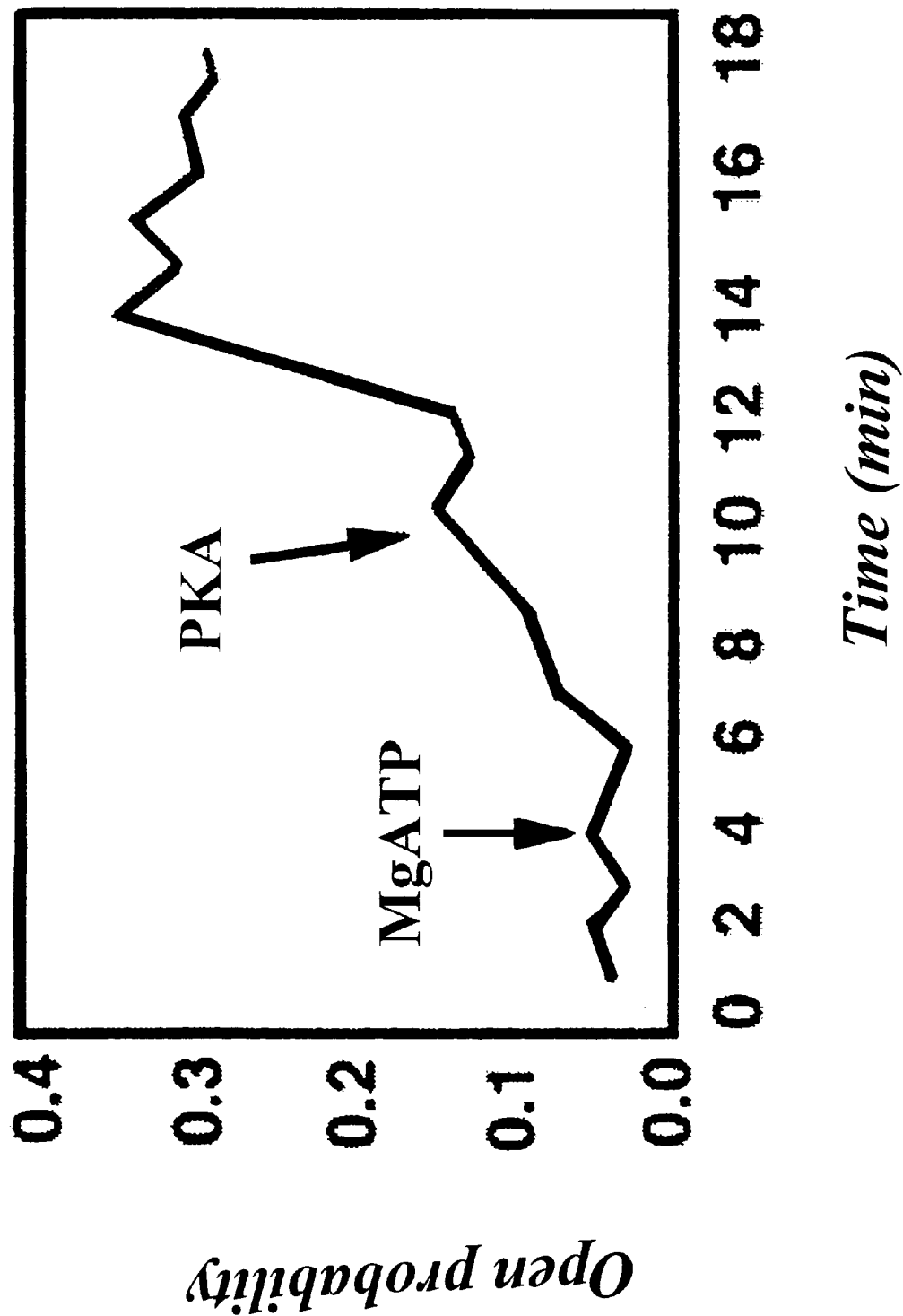
Figure 5B:
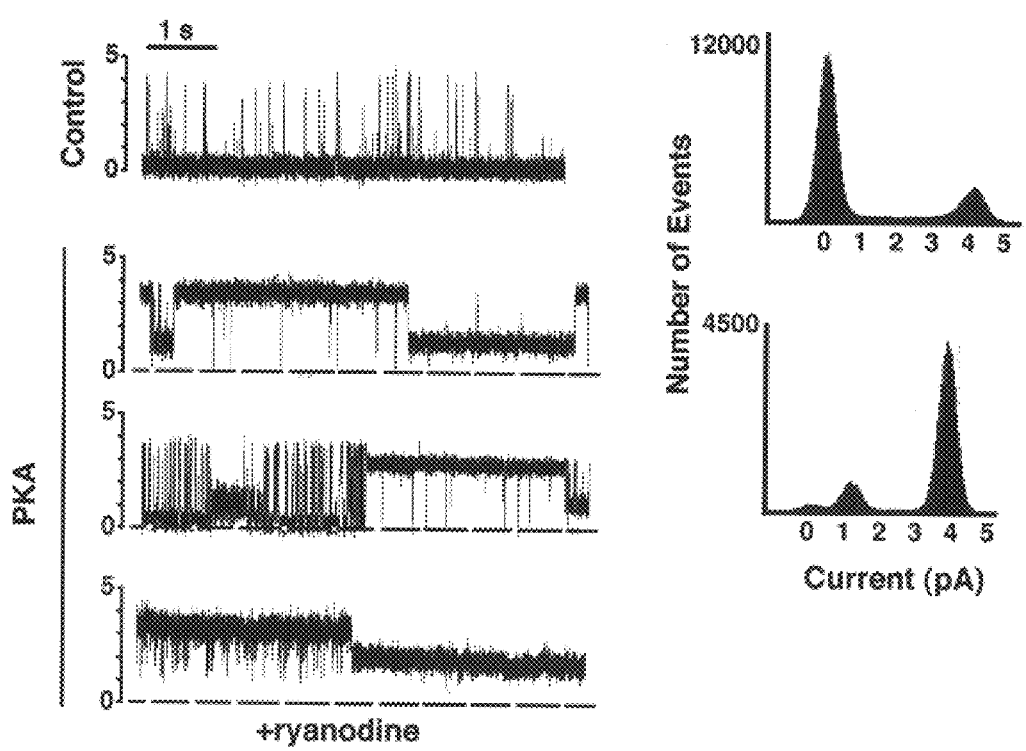

PKA Phosphorylation of RyR2 Increases $P_o$ and Induces Subconductance States. The dissociation of FKBP12/12.6 from RyR1 or RyR2 has previously been shown to increase the channel open probability ($P_o$) by shifting the $Ca^{2+}$-dependence for activation to the left (Brillantes et al., 1994; Kaftan et al., 1996). A second effect of dissociation of FKBP12/12.6 from the channels is to induce subconductance states consistent with a destabilization of the tetrameric channel structure (Brillantes et al. , 1994). PKA phosphorylation of RyR2 in planar lipid bilayers resulted in a significant increase in Po from 0.10±0.03 to 0.35±0.06 (n=4/4, p<0.001, e.g. FIG. 5A). PKA phosphorylation of RyR2 also induced subconductance states (n=4, e.g. FIG. 5B) similar to those seen after dissociation of FKBP from the RyR channels (Brillantes et al., 1994; Kaftan et al., 1996; Marx et al., 1998). PKA phosphorylation of RyR2 channels did not alter the mean open time of the full conductance state (for control channels $\tau_o$=2.1±0.8 ms vs. 2.6±0.6 ms following PKA treatment, n=4, p=NS). However, long lasting subconductance states ($\tau_o$=502.1±40.8 ms) were observed following PKA phosphorylation of RyR2 channels in the bilayer (FIG. 5B) . In addition, the phosphatase inhibitor okadaic acid (1 μM) significantly increased RyR2 Po fro m 0.3±0.1 to 0.8±0.1, n=5/6, p<0.001). These data suggest that the mechanism by which PKA phosphorylation activates RyR2 channels involves dissociation of FKBP12.6 from the channel resulting in increased sensitivity to $Ca^{2+}$-induced activation.

Heart Failure and PKA Hyperphosphorylation Produce the Same RyR2 Defects. Single channel recordings of RyR2 channels from human hearts (n=21, 13 channels from 3 patients with heart failure including 3 channels from pre-LVAD treatment heart samples, 4 channels from non-failing hearts, and 4 channels from hearts post-LVAD treatment) and canine hearts (n=27, 14 channels from 2 dogs with pacing-induced heart failure, and 13 channels from non-failing hearts) revealed that the RyR2 channels from failing hearts exhibited the same alterations in single channel properties (FIGS. 6A and 6B) as the PKA phosphorylated channels (FIG. 5B). RyR2 channels from failing hearts exhibited an increased $P_o$ at low cis (cytosolic) $Ca^{2+}$ concentration (50 nM, 0.24±0.21 versus 0.002±0.001, n=27 failing hearts, n=21 non-failing and post-LVAD hearts, p<0.0001). At 50 nM cis (cytosolic) [$Ca^{2+}$], 70% of the RyR2 channels from failing hearts (19/27) exhibited increased $P_o$ ($P_o$>0) compared with 9.5% (2/21) channels from non-failing hearts. Moreover, there were two types of behavior exhibited by RyR2 channels that were active at 50 nM cis (cytosolic) [$Ca^{2+}$]. Fifty-six % of RyR2 channels from failing hearts exhibited low levels of activity (n=15/27, $P_o$ 0.03), which is abnormal as channels from non-failing hearts are almost always completely inactive at 50 nM cis (cytosolic) [$Ca^{2+}$] (FIG. 6B) Strikingly, 15% of the RyR2 channels from failing hearts (n=4/27) exhibited a second type of behavior that was never observed in channels from normal hearts: a long lasting subconductance state at 50 nM cis (cytosolic) [$Ca^{2+}$] with $P_o \simeq 1.0$ (FIG. 6B) similar to those observed following PKA phosphorylation of RyR2 channels in the bilayer (e.g. see FIG. 5B). These subconductance states had markedly increased open times ($\tau_o$=802.1±66.7 ms) compared to the RyR2 channels from non-failing hearts ($\tau_o$=2.2±0.7 ms) (e.g. see FIG. 6B). RyR2 channels that are active at 50 nM cis (cytosolic) [$Ca^{2+}$] would be expected to be open throughout the cardiac cycle (both in systole and diastole).

Figure 6A:
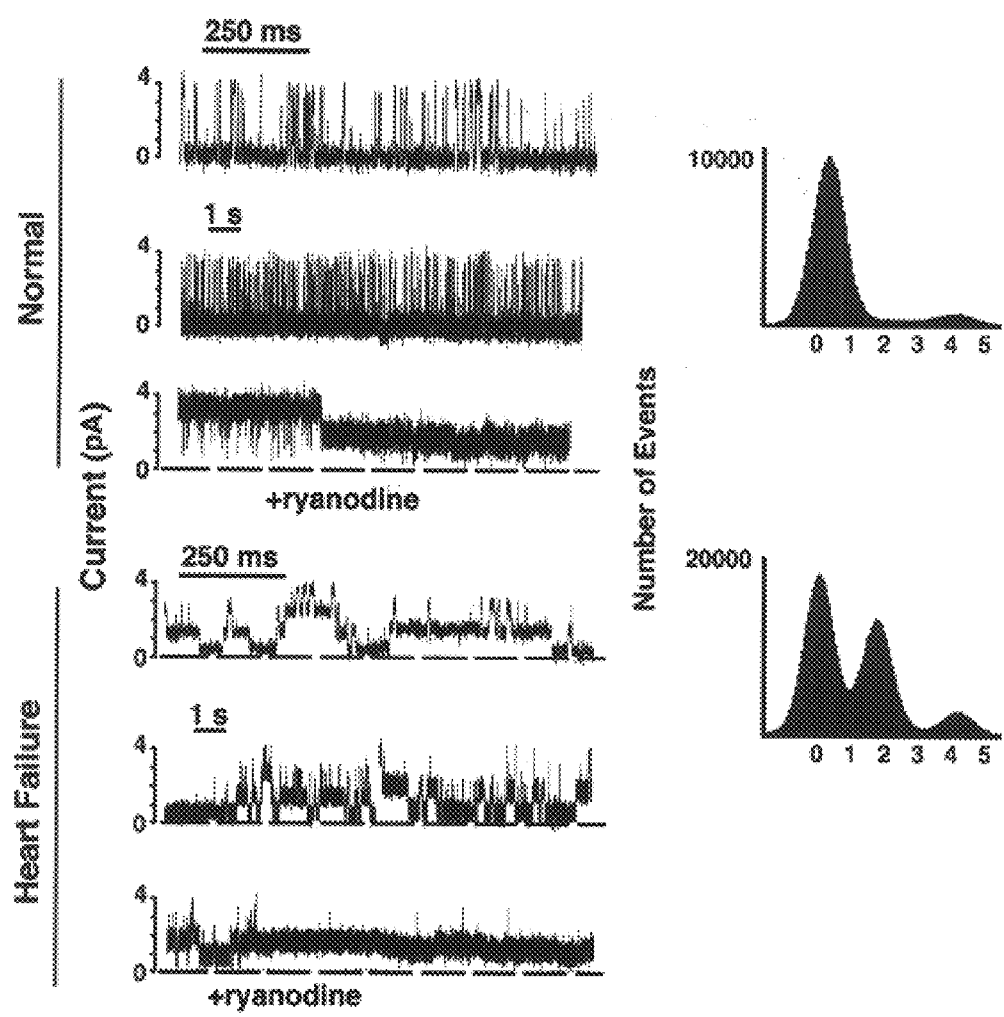
Figure 6C:
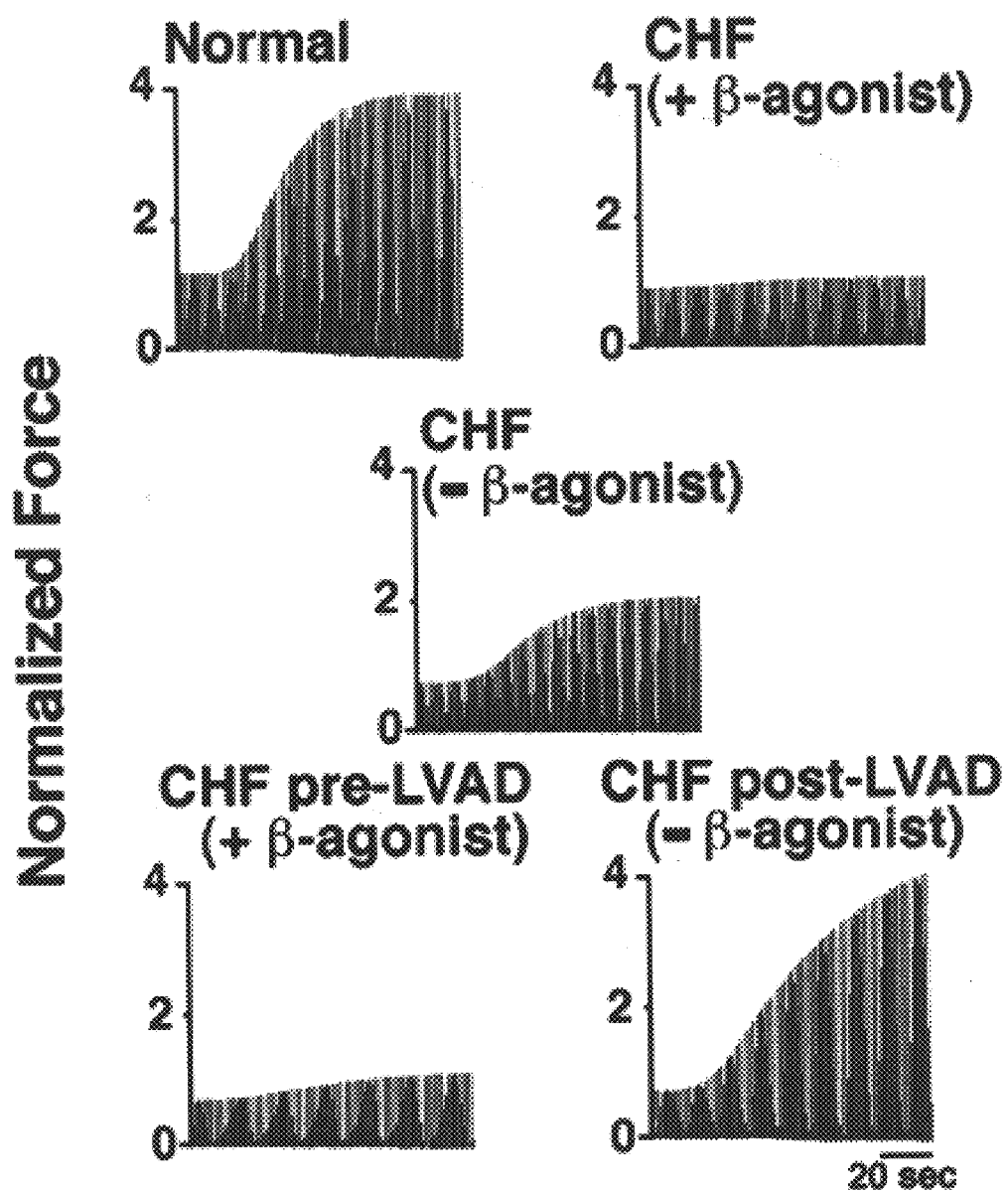

In 52% of RyR2 channels from failing hearts subconductance states were observed (n=14/27) that were present in less than 5% of channels from normal hearts (n=1/21, p<0.001) (e.g. see FIG. 6A). The subconductance states are similar to those observed when RyR1 channels are expressed without FKBP12 (Brillantes et al., 1994) or when FKBP12.6 is dissociated from native RyR2 channels (Kaftan et al., 1996) and in PKA phosphorylated channels (FIG. 5A). As noted above channels from failing hearts also exhibited increased PKA phosphorylation (FIGS. 2A and 2B) and reduced FKBP12.6 binding (FIG. 4B). These data suggest that increased PKA phosphorylation of RyR2 in failing hearts results in dissociation of FKBP12.6 which causes defects in the single channel properties characterized by subconductance states and increased $P_o$ consistent with destabilized channels and altered $Ca^{2+}$ sensitivity (Brillantes et al., 1994).

β-Adrenergic Agonist Response Restored by LVAD Treatment. Physiologic levels of PKA phosphorylation of RyR2 would increase SR $Ca^{2+}$ release resulting in increased cardiac muscle contractility that explains, at least in part, the inotropic effects of β-adrenergic agonists. The blunting of the β-adrenergic agonist-induced increase in cardiac contractility in failing hearts has been attributed to the downregulation and desensitization of β-adrenergic receptors in failing hearts (Bristow et al., 1992).

The blunted response to β-adrenergic agonists may in part be explained by the fact that in failing heart muscle RyR2 channels are already hyperphosphorylated (FIGS. 2A and 2B) and further PKA phosphorylation of RyR2 cannot occur. Interventions that decrease PKA phosphorylation of RyR2 back towards the levels observed in non-failing hearts should restore β-adrenergic agonist induced increases in cardiac contractility. To test this hypothesis we used muscle strips isolated from pre- and post-LVAD hearts placed in organ baths under conditions such that isoproterenol-induced contraction could be determined. Compared to normal hearts, the pre-LVAD (failing) muscle strips exhibited a blunted response to isoproterenol (FIG. 6C) which was significantly restored following LVAD treatment. LVAD treatment restores PKA phosphorylation of RyR2 to normal levels (FIGS. 2A and 2B) and reverses the defect in single channel properties of RyR2/$Ca^{2+}$ release channels (data not shown). These data suggest that restoration of sensitivity to β-adrenergic agonists observed in the post-LVAD muscle may be explained in part by the increased availability of these RyR2 channels to be physiologically PKA phosphorylated.

Discussion

The present application discloses that PKA phosphorylation regulates FKBP12.6 binding to RyR2 providing a mechanism for modulating the sacroplasmic reticulum $Ca^{2+}$ release channel required for excitation-contraction coupling. PKA hyperphosphorylation of RyR2 in failing hearts resulted in the following abnormal single channel properties: 1) increased $Ca^{2+}$ sensitivity for activation; and 2) elevated channel activity ($P_o$) associated with destabilization of the tetrameric channel complex (manifested as subconductance states including long lasting partially open states never observed in channels from non-failing hearts). Co-sedimentation and co-immunoprecipitation studies were used to define an RyR2 channel macromolecular complex that includes FKBP12.6, PKA, RII, PP1 and PP2A, and mAKAP suggesting that phosphorylation of the channel is locally controlled (FIG. 7). FKBP12.6 and FKBP12 are integral components of the cardiac muscle RyR2 and skeletal muscle RyR1 SR $Ca^{2+}$ release channels, respectively (Jayaraman et al., 1992; Marks, 1996) and are required for normal channel gating (Brillantes et al., 1994; Kaftan et al., 1996; Marx et al., 1998). Dissociation of FKBP12/12.6 from RyR1 or RyR2 results in three defects in channel function: 1) subconductance states with conductances equal to ¼, ½ and ¾ of the fully open channel; 2) increased $P_o$; and 3) increased sensitivity to $Ca^{2+}$-dependent activation (Brillantes et al., 1994; Kaftan et al., 1996; Marx et al., 1998). The increased $P_o$ exhibited in channels following removal of FKBP12/12.6 is explained by the increased sensitivity to $Ca^{2+}$-dependent activation (Brillantes et al., 1994) which represents a shift to the left of the ascending portion of the bell-shaped curve describing the $Ca^{2+}$-dependence of the RyR channels (Bezprozvanny et al., 1991). Increased $P_o$ at low cytosolic $Ca^{2+}$ (e.g. 50 nM [$Ca^{2+}$] see FIG. 6B) would result in inappropriately active SR $Ca^{2+}$ release channels. This would lead to depletion of SR $Ca^{2+}$ that might impair systolic function of the heart (by diminishing the $Ca^{2+}$ signal that activates muscle contraction). Inappropriate SR $Ca^{2+}$ release channel activation at low cytosolic $Ca^{2+}$ might also contribute to early and delayed after depolarizations that trigger fatal cardiac arrhythmias and cause sudden cardiac death (Fozzard, 1992).

Alterations in RyR2 single channel function induced by PKA phosphorylation, correspond to those observed when FKBP12.6 is dissociated from the channel (FIGS. 5A and 5B). In agreement with our findings it has been reported that PKA phosphorylation of RyR2 increases the activity of the channel (Hain et al., 1995; Valdivia et al., 1995). RyR2 channels isolated from failing hearts were PKA hyperphosphorylated (FIGS. 2A and 2B) and exhibited the same alterations in function observed in in vitro PKA phosphorylated channels (FIGS. 6A and 6B). Taken together these data show that PKA hyperphosphorylation of RyR2 in failing hearts causes a defect in channel function due to the dissociation of the regulatory subunit FKBP12.6. Treatment of heart failure with a mechanical device (LVAD) that improves heart function was associated with a decrease in RyR2 PKA phosphorylation to levels observed in normal human hearts (FIGS. 2A and 2B). In addition LVAD treatment resulted in normalized RyR2 single channel function (i.e. reduction in subconductance states, normalization of the $Ca^{2+}$ sensitivity for activation and decreased $P_o$).

An additional effect of dissociation of FKBP12 from RyR1 is to uncouple gating of neighboring channels (Marx et al., 1998). We have recently found that FKBP12.6 is required for coupled gating between RyR2 channels. Coupled gating provides a mechanism whereby all of the RyR2 channels in a T-tubule/SR junction can be uniformly activated resulting in an optimal $Ca^{2+}$ signal to trigger cardiac muscle contraction. One consequence of uncoupling RyR2 channels would be a loss of excitation-contraction coupling gain which has been observed experimentally in cardiomyopathic hearts (Gomez et al., 1997).

The present application discloses that muscle A kinase anchoring protein (mAKAP), which has been localized to cardiac SR as well as the perinuclear region (McCartney et al., 1995; Yang et al., 1998), co-sediments and co-immunoprecipitates with RyR2. mAKAP could bind directly to RyR2, similar to yotia which binds directly to the NMDA receptor (Westphal et al., 1999), or via an adaptor. The PKA regulatory subunit RII binds directly to AKAPs (Fraser and Scott, 1999) and anchors the PKA catalytic subunit. PP1 and PP2A may interact with RyR2 directly or via their own regulatory/targeting proteins possibly by binding to leucine/isoleucine zippers present in RyR2.

β-adrenergic signaling cascade components (the stimulatory G-protein Gs and adenylyl cyclase) have been localized to the transverse tubular network in rat ventricular myocytes (Laflamme and Becker, 1999). Thus, one important consequence of anchoring PKA, RII, PP1 and PP2A to the RyR2 complex and localizing upstream components of the β-adrenergic signaling cascade to the T-tubule-SR junction is that phosphorylation/dephosphorylation of RyR2 can be regulated locally at the site of excitation-contraction coupling.

The stoichiometry of PKA back-phosphorylation for the channels from failing hearts was 0.7 (compared to 3.8 for fully dephosphorylated channels and 3.1 for RyR2 from non-failing hearts) indicating that approximately three of the four PKA sites on RyR2 were phosphorylated in failing hearts compared to one or none on RyR2 from non-failing hearts. RyR2 PKA hyperphosphorylation explains the ~60% decrease in the amount of FKBP12.6 bound to the RyR2 channels from failing hearts compared to channels from normal hearts (FIG. 4B). This decrease in FKBP12.6 binding to RyR2 channels may account for the ~70% of RyR2 channels from failing hearts that exhibited altered single channel properties similar to those observed when FKBP12.6 is competed off from the channel using rapamycin or FK506 (Brillantes et al., 1994; Kaftan et al., 1996; Marx et al., 1998). Moreover, 15% of channels from failing hearts exhibited the most severe defect (long lasting subconductance states with Po≃1 at 50 nM cytosolic $[Ca^{2+}]$, e.g. FIG. 6B) suggesting that these channels have one or no FKBP12.6 bound.

Heart failure is the leading cause of mortality and morbidity in the United States, accounting for ~400,000 deaths annually with ~50% of these deaths caused by disturbances in the cardiac rhythm referred to as sudden cardiac death (SCD). A common feature of human heart failure and of many animal models of heart failure is a hyperadrenergic state, and elevated levels of circulating catecholamines are a marker for increased mortality in heart failure patients (Cohn et al., 1984).

Studies demonstrating down regulation of β-adrenergic receptors in failing heart muscle and desensitization of these receptors attributable to uncoupling from their downstream signaling molecules, G-proteins (Bristow et al., 1982), have led to some confusion since β-adrenergic blockers have proven to be one of the most important treatments for heart failure (CIBIS-II, 1999; MERIT-HF, 1999). Several studies have reported that cAMP levels and PKA activity are unchanged in failing human hearts (Kirchhefer et al., 1999; Regitz-Zagrosek et al., 1994) or that cAMP levels are reduced but PKA activity is unchanged (Bohm et al., 1994). The use of β-adrenergic blockers has been viewed as counterintuitive since the adrenergic system has been thought to be down regulated in failing hearts and drugs with negative inotropic properties are considered potentially dangerous to patients. Therefore, a mechanistic understanding of the molecular basis for the therapeutic benefit afforded by β-adrenergic blockers in patients with heart failure would be an important advance in the approach to this disease. Experiments in progress demonstrate that β-adrenergic blockers reverse the PKA hyperphosphorylation of RyR2 in dogs with heart failure induced by rapid cardiac pacing.

The present study shows that the sacroplasmic reticulum $Ca^{2+}$ release channel RyR2 is unexpectedly PKA hyperphosphorylated in failing hearts. These data raise for the first time the concept that local signaling may increase rather than decrease phosphorylation of PKA substrates in cardiomyocytes from failing hearts.

One explanation for the surprising finding of PKA hyperphosphorylation of RyR2 is that targeting of phosphatases to RyR2 may be downregulated in failing hearts. Indeed, we found that the levels of PP1 and PP2A associated with RyR2 were significantly decreased in failing hearts (FIGS. 2C and 2D). Cellular PP1 levels are increased in failing hearts (Neumann et al., 1997); thus, the decrease in RyR2-associated PP1 must be due to a specific decrease in PP1 association with RyR2 that cannot be explained by a generalized decrease in PP1 levels in the heart.

Defects in $Ca^{2+}$ regulation that could explain the decreased contractility observed in failing hearts, including a reduced amplitude and slowed decay of the $Ca^{2+}$ transient, have been described (Beuckelmann et al., 1992; Morgan et al., 1990). However, the molecular basis for these defects has not been elucidated. The release and reuptake of $Ca^{2+}$ from the sacroplasmic reticulum controls the force of contraction during systole in the heart. SR $Ca^{2+}$ release occurs via activation of RyR2, and $Ca^{2+}$ reuptake occurs via the SR Ca 2+-ATPase which in turn is regulated by phospholamban. PKA has multiple substrates in cardiomyocytes including phospholamban, the L-type $Ca^{2+}$ channel on the sarcolemma and components of the contractile apparatus. It has been appreciated for some time that β-adrenergic agonists can modulate the activity of molecules involved in regulating cardiac contractility. Clearly, a disease as complex as heart failure involves an interplay between a number of molecules and signaling pathways that contribute to the regulation of $Ca^{2+}$ homeostasis. One key point distinguishing the present study is the identification of a functional defect in a $Ca^{2+}$ handling molecule that occurs not only in animal models (e.g. the paced dog model) but also in human failing hearts and is reversed by treatment of the heart failure (e.g. with an LVAD) in humans.

The present application discloses that protein kinase A (PKA) phosphorylation of the cardiac rynaodine receptor/calcium release channel (RyR2) on serine 2809 activates the channel by releasing the FK-506 binding protein 12.6 (FKBP12.6). In failing hearts (human as well as animal models of heart failure) RyR2 is PKA hyperphosphorylated resulting in defective channels that have decreased amounts of FKBP12.6 bound to them and have increased sensitivity to calcium-induced activation. The net result of these changes is that the RyR2 channels are "leaky". These "leaky" channels can result in depletion of intracellular stores of calcium such that there is not enough calcium in the sarcoplasmic reticulum to provide a strong stimulus for muscle contraction. This results in weak contraction of heart muscle. A second consequence of the "leaky" RyR2 channels is that they release calcium during the resting phase of the heart cycle known as diastole. This release of calcium during diastole can trigger fatal arrhythmias of the heart (e.g., ventricular tachycardia and ventricular fibrillation) that cause sudden cardiac death.

The application discloses a novel mechanism for modulating RyR2 channel function by physiologically controlling the binding of FKBP12.6 to the channel via PKA phosphorylation. Furthermore, the finding of PKA hyperphosphorylated channels with defective function in failing hearts provides a mechanism for cardiac dysfunction in heart failure. The application discloses novel targets for controlling heart muscle contraction and for treating heart failure. In addition, the application discloses methods for testing new therapeutic approaches to heart disease by assaying their effects on the RyR2 channel.

REFERENCES

Beuckelmann, D., Nabauer, M., and Erdmann, E. (1992). Intracellular calcium handling in isolated ventricular myocytes from patients with terminal heart failure. Circ. 85, 1046–1055.

Bezprozvanny, I., Watras, J., and Ehrlich, B. (1991). Bell-shaped calcium response curves of Ins(1,4,5)P3-and calcium-gated channels from endoplasmic reticulum of cerebellum. Nature 351, 751–754.

Bohm, M., Reiger, B., Schwinger, R. H., and Erdmann, E. (1994). cAMP concentrations, cAMP dependent protein kinase activity, and phospholamban in non-failing and failing myocardium. Cardiovasc Res 28, 1713–9.

Brillantes, A. B., Ondrias, K., Scott, A., Kobrinsky, E., Ondriasova, E., Moschella, M. C., Jayaraman, T., Landers, M., Ehrlich, B. E., and Marks, A. R. (1994). Stabilization of calcium release channel (ryanodine receptor) function by FK506-binding protein. Cell 77, 513–23.

Bristow, M. R., Ginsburg, R., Minobe, W., Cubicciotti, R. S., Sageman, W. S., Lurie, K., Billingham, M. E., Harrison, D. C., and Stinson, E. B. (1982). Decreased catecholamine sensitivity and beta-adrenergic-receptor density in failing human hearts. N. Engl. J. Med. 307, 205–211.

Bristow, M. R., Minobe, W., Rasmussen, R., Larrabee, P., Skerl, L., Klein, J. W., Anderson, F. L., Murray, J., Mestroni, L., Karwande, S. V., and et al. (1992). Beta-adrenergic neuroeffector abnormalities in the failing human heart are produced by local rather than systemic mechanisms. J Clin Invest 89, 803–15.

Cameron, A. M., Nucifora, F. C., Jr., Fung, E. T., Livingston, D. J., Aldape, R. A., Ross, C. A., and Snyder, S. H. (1997). FKBP12 binds the inositol 1,4,5-trisphosphate receptor at leucine-proline (1400–1401) and anchors calcineurin to this FK506-like domain. J Biol Chem 272, 27582–8.

Chen, Y. G., Liu, F., and Massague, J. (1997). Mechanism of TGFbeta receptor inhibition by FKBP12. EMBO J 16, 3866-76. CIBIS-II (1999). The Cardiac Insufficiency Bisoprolol Study II (CIBIS-II): a randomised trial. Lancet 353, 9–13.

Cohn, J. N., Levine, T. B., Olivari, M. T., Garberg, V., Lura, D., Francis, G. S., Simon, A. B., and Rector, T. (1984). Plasma norepinephrine as a guide to prognosis in patients with chronic congestive heart failure. N Engl J Med 311, 819–23.

Fozzard, H. A. (1992). After depolarizations and triggered activity. Basic Res Cardiol 87, 105–113.

Franzen, P., ten Dijke, P., Ichijo, H., Yamashita, H., Schulz, P., Heldin, C.H. and Miyazono, K. (1993). Cloning of a TGF beta type I receptor that forms a heteromeric complex with the TGF beta type II receptor. Cell 75 (4), 681–692.

Fraser, I. D., and Scott, J. D. (1999). Modulation of ion channels: a "current" view of AKAPs. Neuron 23, 423–6.

Frazier, O. H. (1994). First use of an untethered, vented electric left ventricular assist device for long-term support. Circulation 89, 2908–14.

Gillo, B., Ma, Y. S. and Marks, A. R. (1993). Calcium entry during induced differentiation in Murine erythroleukemia cells. Blood 81, 783–792.

Go, L. O., Moschella, M. C., Watras, J., Handa, K. K., Fyfe, B. S., and Marks, A. R. (1995). Differential regulation of two types of intracellular calcium release channels during end-stage heart failure. J Clin Invest 95, 888–94.

Gomez, A. M., Valdivia, H. H., Cheng, H., Lederer, M. R., Santana, L. F., Cannell, M. B., McCune, S. A., Altschuld, R. A., and Lederer, W. J. (1997). Defective excitation-contraction coupling in experimental cardiac hypertrophy and heart failure. Science 276, 800–6.

Hain, J., Onoue, H., Mayrleitner, M., Fleischer, S., and Schindler, H. (1995). Phosphorylation modulates the function of the calcium release channel of sarcoplasmic reticulum from cardiac muscle. J Biol Chem 270, 2074–81.

Harnick, D. J., Jayaraman, T., Ma, Y., Mulieri, P., Go, L. O. and Marks, A. R. (1995). The human type 1 inositol 1,4,5-trisphosphate receptor from T lymphocytes. Structure, localization, and tyrosine phosphorylation. J. Biol. Chem. 270 (6), 2833–2840.

Jayaraman, T., Brillantes, A.-M. B., Timerman, A. P., Erdjument-Bromage, H., Fleischer, S., Tempst, P., and Marks, A. R. (1992). FK506 Binding Protein Associated with the Calcium Release Channel (Ryanodine Receptor). J. Biol. Chem. 267, 9474–9477.

Jayaraman, T., Ondrias, K., Ondriasova, E. and Marks, A. R. (1996). Regulation of the inositol 1,4,5-trisphosphate receptor by tyrosine phosphorylation. Science 272, 1492–1494.

Kaftan, E., Marks, A. R., and Ehrlich, B. E. (1996). Effects of rapamycin on ryanodine receptor/Ca$^{(2+)}$-release channels from cardiac muscle. Circ Res 78, 990–7.

Kapiloff, M. S., Schillace, R. V., Westphal, A. M., and Scott, J. D. (1999). mAKAP: an A-kinase anchoring protein targeted to the nuclear membrane of differentiated myocytes. J Cell Sci 112, 2725–36.

Kirchhefer, U., Schmitz, W., Scholz, H., and Neumann, J. (1999). Activity of cAMP-dependent protein kinase and Ca2+/calmodulin-dependent protein kinase in failing and nonfailing human hearts. Cardiovasc Res 42, 254–61.

Laflamme, M. A., and Becker, P. L. (1999). Gs and adenylyl cyclase in transverse tubules of heart: implications for cAMP-dependent signaling. Am. J. Phys. 277, H1841–H1848.

Levin, H. R., Oz, M. C., Chen, J. M., Packer, M., Rose, E. A., and Burkhoff, D. (1995). Reversal of chronic ventricular dilation in patients with end-stage cardiomyopathy by prolonged mechanical unloading. Circulation 91, 2717–20.

Lorenz, M. C., and Heitman, J. (1995). TOR mutations confer rapamycin resistance by preventing interaction with FKBP12-rapamycin. J Biol Chem 270, 27531–27537.

MacDougall, L. K., Jones, L. R., and Cohen, P. (1991). Identification of the major protein phosphatases in mammalian cardiac muscle which dephosphorylate phospholamban. European Journal of Biochemistry 196, 725–34.

Marks, A. R. (1996). Cellular functions of immunophilins. Physiol. Rev. 76, 631–49.

Marx, S. O., Ondrias, K., and Marks, A. R. (1998). Coupled gating between individual skeletal muscle Ca$^{2+}$ release channels (ryanodine receptors). Science 281, 818–21.

McCartney, S., Little, B. M., Langeberg, L. K., and Scott, J. D. (1995). Cloning and characterization of A-kinase anchor protein 100 (AKAP100). A protein that targets A-kinase to the sarcoplasmic reticulum. J Biol Chem 270, 9327–33.

Merit, H. F. (1999). Effect of metoprolol CR/XL in chronic heart failure: Metoprolol CR/XL Randomised Intervention Trial in Congestive Heart Failure (MERIT-HF). Lancet 353, 2001–7.

Morgan, J., Erny, R., Allen, P., Grossman, W., and Gwathmey, J. (1990). Abnormal intracellular calcium handling: a major cause of systolic and diastolic dysfunction in ventricular myocardium from patients with end-stage heart failure. Circulation 81 (suppl III), III21–III32.

Moschella, M. C., and Marks, A. R. (1993). Inositol 1,4,5-trisphosphate receptor expression in cardiac myocytes. J. Cell. Biol. 120, 1137–1146.

Neumann, J., Eschenhagen, T., Jones, L. R., Linck, B., Schmitz, W., Scholz, H., and Zimmermann, N. (1997). Increased expression of cardiac phosphatases in patients with end-stage heart failure. J Mol Cell Cardiol 29, 265–72.

Otsu, K., Willard, H. F., Khanna, V. K., Zorato, F., Green, N. M. and MacLennan, D. H. (1990). Molecular cloning of cDNA encoding the Ca-2+ release channel (ryanodine receptor) of rabbit cardiac muscle sarcoplasmic reticulum. J. Biol. Chem. 265, 13472–13483.

Regitz-Zagrosek, V., Hertrampf, R., Steffen, C., Hildebrandt, A., and Fleck, E. (1994). Myocardial cyclic AMP and norepinephrine content in human heart failure. Eur Heart J 15 Suppl D, 7-13.

Takeshima, H., Nishimura, S., Matsumoto, T., Ishido, H., Kangawa, K., Minamino, N., Matsuo, H., Ueda, M., Hanaoka, H., Hirose, T. and Numa, S. (1989). Primary structure and expression from complementary DNA of skeletal muscle ryanodine receptor. Nature 339 (6224), 439–445.

Valdivia, H. H., Kaplan, J. H., Ellis-Davies, G. C., and Lederer, W. J. (1995). Rapid adaptation of cardiac ryanodine receptors: modulation by Mg2+ and phosphorylation. Science 267, 1997–2000.

Wang, J., Yi, G. H., Knecht, M., Cai, B. L., Poposkis, S., Packer, M., and Burkhoff, D. (1997). Physical training alters the pathogenesis of pacing-induced heart failure through endothelium-mediated mechanisms in awake dogs. Circulation 96, 2683-92.

Westphal, R. S., Tavalin, S. J., Lin, J. W., Alto, N. M., Fraser, I. D., Langeberg, L. K., Sheng, M., and Scott, J. D. (1999). Regulation of NMDA receptors by an associated phosphatase-kinase signaling complex. Science 285, 93–6.

Yamamoto-Hino, M., Sugiyama, T., Hikiti, K., Mattei, M.G., Hasegawa, K., Sekine, S., Sakurada, K., Miyawaki, A., Furuichi, T., Hasegawa, M. and Mikoshiba, K. (1994). Cloning and characterization of human type 2 and type 3 inositol 1,4,5-trisphosphate receptors. Recept. Channels 2 (1), 9–22.

Yang, J., Drazba, J. A., Ferguson, D. G., and Bond, M. (1998). A-kinase anchoring protein 100 (AKAP100) is localized in multiple subcellular compartments in the adult rat heart. J Cell Biol 142, 511–22.

What is claimed is:

1. A method for identifying a chemical compound that inhibits dissociation of a FKBP12.6 binding protein from a type 2 ryanodine (RyR2) receptor, which comprises separately contacting cells expressing the RyR2 receptor, or separately contacting sacroplasmic reticulum or endoplasmic reticulum from an extract from said cells, with both the chemical compound and a second chemical compound known to cause dissociation of the FKBP12.6 binding protein from the RyR2 receptor, and with only the second chemical compound, under conditions suitable for dissociation of the FKBP12.6 binding protein from the RyR2 receptor, and measuring dissociation of the FKBP12.6 binding protein from the RyR2 receptor in the presence of only the second chemical compound and in the presence of both the second chemical compound and the chemical compound, a smaller dissociation of the FKBP12.6 binding protein from the RyR2 receptor in the presence of both the chemical compound and the second chemical compound than in the presence of only the second chemical compound indicating that the chemical compound inhibits dissociation of the FKBP12.6 binding protein from the RyR2 receptor.

2. The method of claim 1, wherein the chemical compound is not previously known to inhibit dissociation of the FKBP12.6 binding protein from the RyR2 receptor.

3. A method of screening a plurality of chemical compounds not known to inhibit dissociation of the FKBP12.6 binding protein from the RyR2 receptor to identify a compound that inhibits dissociation of the FKBP12.6 binding protein from the RyR2 receptor, which comprises:

(a) contacting cells expressing the RyR2 receptor, or contacting sacroplasmic reticulum or endoplasmic reticulum from an extract from said cells, with the plurality of compounds in the presence of a compound known to cause dissociation of the FKBP12.6 binding protein from the RyR2 receptor, under conditions permitting dissociation of the FKBP12.6 binding protein from the RyR2 receptor;

(b) determining whether the amount of dissociation of the FKBP12.6 binding protein from the RyR2 receptor is reduced in the presence of one or more of the compounds, relative to the amount of dissociation of the FKBP12.6 binding protein in the absence of such one or more compounds; and if so (c) separately determining whether each such compound inhibits dissociation of the FKBP12.6 binding protein from the RyR2 receptor for each compound in the plurality of compounds, so as to thereby identify any compound in such plurality of compounds that inhibits dissociation of the FKBP12.6 binding protein from the RyR2 receptor.

4. The method of claim 1 or 3, wherein the measurement of the dissociation of the FKBP12.6 binding protein from the RyR2 receptor comprises measuring protein kinase A phosphorylation of the RyR2 receptor.

5. The method of claim 4, wherein the measurement of protein kinase A phosphorylation of the RyR2 receptor comprises using an antibody that is specific for the phosphorylated form of the RyR2 receptor.

6. The method of claim 1 or 3, wherein the RyR2 receptor is a human RyR2 receptor.

7. The method of claim 1 or 3, wherein the nucleic acid encoding the RyR2 receptor is endogenous to the cell.

8. The method of claim 1 or 3, wherein the nucleic acid encoding the RyR2 receptor is transfected into the cell.

9. The method of claim 8, wherein the cell is a bacterial cell, a yeast cell, an insect cell, an amphibian cell, a plant cell or a mammalian cell.

10. The method of claim 9, wherein the mammalian cell is a HEK293 cell, a Chinese hamster ovary (CHO) cell, a COS-7 cell, a LM(tk-) cell, a mouse embryonic fibroblast NIH-3T3 cell, a mouse Y1 cell, a 293 human embryonic kidney cell, or a HeLa cell.

11. The method of claim 9, wherein the insect cell is an Sf9 cell, an Sf21 cell or a Trichoplusia ni 5B-4 cell.

12. The method of claim 9, wherein the amphibian cell is a Xenopus oocyte cell or a Xenopus melanophore cell.

13. The method of claim 1 or 3, wherein the cells are cardiac cells from a subject with a failing heart.

14. The method of claim 13, wherein the subject is an animal in which heart failure has been induced by rapid cardiac pacing or a human.

15. A method for preparing a composition which comprises identifying a chemical compound by the method of claim 1 or 3, and admixing a carrier and a pharmaceutically effective amount of the chemical compound.

16. A method for preparing a composition which comprises identifying a chemical compound by the method of claim 1 or 3, and admixing a carrier and the chemical compound.

17. The method of claim 1 or 3, wherein the measurement of the dissociation of the FKBP12.6 binding protein from the RyR2 receptor comprises measuring the release of calcium via the RyR2 receptor using a calcium-sensitive fluorescent dye.

* * * * *